United States Patent
Cai et al.

(10) Patent No.: US 6,423,711 B1
(45) Date of Patent: *Jul. 23, 2002

(54) HETEROCYCLIC AMINO SUBSTITUTED HETEROARYL FUSED PYRIDINES; GABA BRAIN RECEPTOR LIGANDS

(75) Inventors: Guolin Cai, Guilford, CT (US); Gang Liu, Agoura, CA (US); Guoquing Chen, North Branford; Pamela A. Albaugh, Clinton, both of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/736,497

(22) Filed: Dec. 13, 2000

Related U.S. Application Data

(63) Continuation of application No. 09/259,146, filed on Feb. 26, 1999, now Pat. No. 6,166,203.
(60) Provisional application No. 60/076,099, filed on Feb. 26, 1998.

(51) Int. Cl.[7] ................... C07D 413/04; C07D 471/02; A61K 31/4365
(52) U.S. Cl. .............................. 514/233.8; 514/253.04; 514/301; 544/127; 544/362; 546/114
(58) Field of Search ................. 544/127, 362; 546/114; 514/233.8, 253.04, 301

(56) References Cited

U.S. PATENT DOCUMENTS 3,985,760 A  * 10/1976  Hoehn et al. ............ 424/250 X
6,166,203 A  * 12/2000  Cai et al. ..................... 544/127

FOREIGN PATENT DOCUMENTS

EP          0168812    * 1/1986
JP          7-196647   * 8/1985

* cited by examiner

*Primary Examiner*—Laura L. Stockton
(74) *Attorney, Agent, or Firm*—McDonnell Boehnen Hulbert & Berghoff

(57) ABSTRACT

Disclosed are compounds of the formula

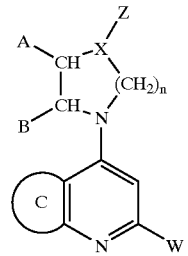

or the pharmaceutically acceptable non-toxic salts thereof wherein:

n is an integer from 0 to 3;

the C ring is aryl or heteroaryl;

X is CH, N, or O

Z represents an electron pair, hydrogen, or (un)substituted heterocycle, aryl, or amido;

W is (un)substituted alkyl, aryl, or heteroaryl;

A and B are hydrogen or lower alkyl, which compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, Down Syndrome, sleep, cognitive and seizure disorders, and overdose with benzodiazepine drugs and for enhancement of alertness.

23 Claims, No Drawings

HETEROCYCLIC AMINO SUBSTITUTED HETEROARYL FUSED PYRIDINES; GABA BRAIN RECEPTOR LIGANDS

This application is a continuation of Ser. No. 29/259,146 which was filed Feb. 26, 1999 and issued as U.S. Pat. No. 6,166,203 which claims benefit of Ser. No. 60/076,099 which was filed Feb. 26, 1998.

BACKGROUND OF THE INVENTION

1. Field of the Invention

This invention relates to heterocyclic amino substituted heteroaryl fused pyridines, and more specifically to such compounds that selectively bind to GABAa receptors. This invention also relates to pharmaceutical compositions comprising such compounds. It further relates to the use of such compounds in treating anxiety, sleep and seizure disorders, and overdoses of benzodiazepine-type drugs, and enhancing alertness. The interaction of heterocyclic amino substituted heteroaryl fused pyridines of the invention with a GABA binding site, the benzodiazepines (BDZ) receptor, is described. This interaction results in the pharmacological activities of these compounds.

2. Description of the Related Art

γ-Aminobutyric acid (GABA) is regarded as one of the major inhibitory amino acid transmitters in the mammalian brain. Over 40 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Drugs that interact at the GABAa receptor can possess a spectrum of pharmacological activities depending on their abilities to modify the actions of GABA.

The 1,4-Benzodiazepines, such as diazepam, continue to be among the most widely used drugs in the world as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. Presently, those compounds possessing activity similar to the benzodiazepines are called agonists. Compounds possessing activity opposite to benzodiazepines are called inverse agonists, and the compounds blocking both types of activity have been termed antagonists.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into α, β, γ, δ, ε, and provide a molecular basis for the GABAa receptor heterogeneity and distinctive regional pharmacology (Shivvers et al., 1980; Levitan et al., 1989). The γ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior. Depending on the mode of interaction, these compounds are capable of producing a spectrum of activities (either sedative, anxiolytic, and anticonvulsant, or wakefulness, seizures, and anxiety).

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in the diagnosis and treatment of anxiety, sleep and seizure disorders, overdose with benzodiazepine drugs and for enhancement of memory. Accordingly, a broad embodiment of the invention is directed to compounds of general Formula I:

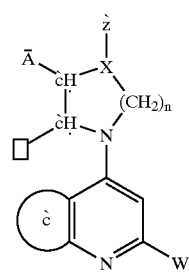

I wherein:
 the C ring represents a thiophene, pyridine, pyrazine, pyridazine, or pyrimidine ring, each of which is optionally mono- or disubstituted with lower alkyl, $C_1$–$C_6$ alkoxy, hydroxy, halogen, amino, mono- or di($C_1$–$C_6$) alkylamino, or trifluoromethyl;
 n is 0 or an integer of from 1–3;
 X is CH, nitrogen, or oxygen;
 Z is an electron pair when X is oxygen;
 Z is hydrogen;
 Z is aryl or heteroaryl, each of which is optionally substituted with one, two or three groups independently selected from lower alkyl, lower alkoxy, amino, mono- or di($C_1$–$C_6$)alkylamlno, or halogen; or

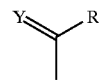

where
 Z is
  Y is oxygen or sulfur;
  R is lower alkyl, hydroxy, lower alkoxy, hydroxyalkyl, or aminoalkyl, or mono- or di($C_1$–$C_6$)alkylamino ($C_1$–$C_6$)alkyl;

R is aryl or heteroaryl each of which is mono or disubstituted independently with halogen, thio, hydroxyl, lower alkyl, lower alkoxy, amino or mono- or di($C_1$–$C_6$)alkylamino;

R is amino, optionally substituted with one or two groups independently selected from
lower alkyl, hydroxyalkyl, $C_3$–$C_7$ cycloalkyl, alkoxyalkyl, aminoalkyl, haloalkyl, hydroxy, aminoalkyl, or amidoalkyl;
heteroaryl, arylalkyl or heteroarylalkyl, optionally substituted with one or two groups independently selected from halogen, thio, hydroxyl, lower alkyl, lower alkoxy, or amino; or
a $C_3$–$C_7$ carbocyclic group having, where up to two of which atoms of the carbocyclic group are optionally hetero atoms selected from oxygen and nitrogen and where any atom of the carbocyclic group is optionally substituted with halogen, lower alkyl or lower alkoxy; or R is a carbocyclic group having from 3–7 members, where up to three of which members are optionally hetero atoms selected from oxygen and nitrogen and where any member of the carbocyclic group is optionally substituted with halogen, lower alkyl, or lower alkoxy;

A and B are the same or different and represent hydrogen or lower alkyl; and

W is aryl or heteroaryl, each of which may be mono-, or di-, or trisubstituted independently with halogen, hydroxyl, lower alkyl, lower alkoxy, amino, mono- or di($C_1$–$C_6$)alkylamino, trifluoromethyl or nitro.

These compounds are highly selective agonists, antagonists or inverse agonists for GABAa brain receptors or prodrugs of agonists, antagonists or inverse agonists for GABAa brain receptors. In other words, while the compounds of the invention all interact with GABAa brain receptors, they do not display identical physiological activity. Thus, these compounds are useful in the diagnosis and treatment of anxiety, sleep and seizure disorders, overdose with benzodiazepine drugs and for enhancement of memory. For example, these compounds can be used to treat overdoses of benzodiazepine-type drugs as they would competitively bind to the benzodiazepine receptor.

DETAILED DESCRIPTION OF THE INVENTION

The novel compounds encompassed by the instant invention can be described by general Formula I set forth above or the pharmaceutically acceptable non-toxic salts thereof.

In addition, the present invention also encompasses compounds of Formula IIa and IIb IIa

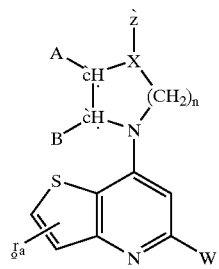

-continued

IIb

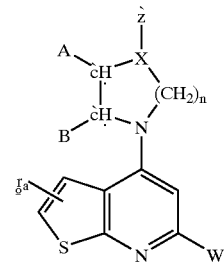

wherein A, B, W, X, Z, and n are as defined above for Formula I; and $R_a$ and $R_b$ independently represent hydrogen, lower alkyl, $C_1$–$C_6$ alkoxy, hydroxy, halogen, amino, mono- or di($C_1$–$C_6$)alkylamino, or trifluoromethyl.

Preferred compounds of Formula IIa and IIb are $R_a$ and $R_b$ are hydrogen, and a where W is phenyl or 2-, 3-, or 4-pyridyl, each of which is optionally mono or disubstituted independently with halogen, hydroxyl, lower alkyl, or lower alkoxy. Other preferred compounds of Formula IIa and IIb are those where X is CH and Z is or 2-imidazolyl, or 1,2,4-triazol-3-yl, Other preferred compounds of the invention are those of Formula II where n is 2 or 3.

Other preferred compounds of Formula IIa and IIb are where A and B are hydrogen or methyl.

Preferred Z groups in Formulae IIa and IIb include Z-1, Z-2, Z-3, Z-4, Z-5, Z-6, Z-7, Z-8, and Z-9 groups.

Z-1

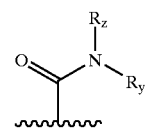

where $R_z$, and $R_y$ are independently hydrogen, $C_1$–$C_6$ alkyl, 2-, 3-, or 4-pyridylmethyl, $C_3$–$C_7$, preferably $C_4$–$C_6$, cycloalkyl, $C_1$–$C_6$ alkoxy($C_1$–$C_6$)alkyl, or 2- or 3-tetrahydrofuranyl($C_1$–$C_6$)alkyl. Preferred $C_1$–$C_6$ alkoxy ($C_1$–$C_6$)alkyl groups are 2-methoxyethyl and 2-ethoxyethyl. Preferred tetrahydrofuranyl-($C_1$–$C_6$)alkyl groups are tetrahydrofuran-2-ylmethyl groups. Particularly preferred Z-1 groups are those where one and only one of $R_z$ and $R_y$ is hydrogen.

Z-2

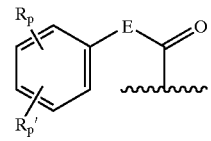

where E is a bond or $C_1$–$C_6$ alkylene, each of Rp and $R_p'$ are independently hydroxy, halogen, $C_1$–$C_6$ alkyl, or $C_1$–$C_6$ alkoxy. Preferred $R_p$ groups are fluoro, more preferably 4-fluoro, and chloro. Preferred $R_p'$ groups are hydrogen, $C_1$–$C_2$ alkoxy, $C_1$–$C_2$ alkyl, fluoro, more preferably 4-fluoro, and chloro. Preferred E groups are a bond and $C_2$ alkylene.

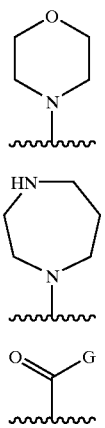

Z-3

Z-4

Z-5 where G is 2-, 3-, or 4-pyridyl, each of which is optionally mono- or disubstituted with $C_1$–$C_6$ alkyl, $C_1$–$C_6$ alkoxy, or halogen.

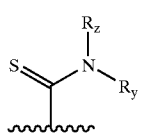

Z-6 where $R_z$ and $R_y$ are independently hydrogen, $C_1$–$C_6$ alkyl, 2-, 3-, or 4-pyridylmethyl, $C_3$–$C_7$, preferably $C_4$–$C_6$, cycloalkyl, $C_1$–$C_6$ alkoxy($C_1$–$C_6$) alkyl, 2-, or 3-tetrahydrofuranyl($C_1$–$C_6$)alkyl. Preferred $C_1$–$C_6$ alkoxy ($C_1$–$C_6$)alkyl groups are 2-methoxyethyl and 2-ethoxyethyl. Preferred tetrahydrofuranyl($C_1$–$C_6$)alkyl groups are tetrahydrofuran-2-ylmethyl groups. Particularly preferred Z-6 groups are those where one and only one of $R_z$ and $R_y$ is hydrogen.

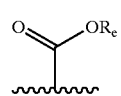

Z-7 where $R_e$ is hydrogen or $C_1$–$C_6$ alkyl. Preferred $R_e$ groups in Z-7 are hydrogen atoms.

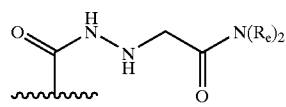

Z-8 where each $R_e$ is independently hydrogen or $C_1$–$C_6$ alkyl. Preferred $R_e$ groups in Z-8 are hydrogen and methyl.

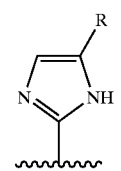

Z-9 where R is $C_1$–$C_6$ alkyl.

The present invention also encompasses compounds of Formula IIIa and Formula IIIb:

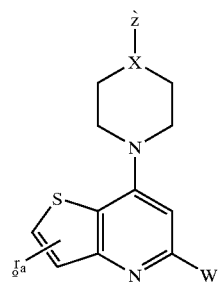

IIIa

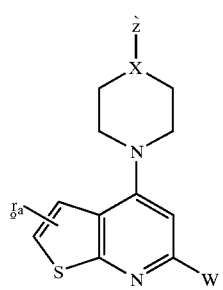

IIIb wherein W, X and Z are as defined above for Formula I; and $R_a$ is hydrogen, lower alkyl, $C_1$–$C_6$ alkoxy, hydroxy, halogen, amino, mono- or di($C_1$–$C_6$)alkylamino, or trifluoromethyl.

Preferred compounds of Formula IIIa and IIIb are where W is phenyl or 2-, 3-, or 4-pyridyl, each of which is optionally mono or disubstituted independently with halogen, hydroxyl, lower alkyl, or lower alkoxy.

Preferred Z groups in Formulae IIIa and IIIb include Z-1, Z-2, Z-3, Z-4, Z-5, Z-6, Z-7, Z-8, and Z-9 groups.

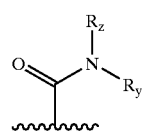

Z-1 where $R_z$ and $R_y$ are independently hydrogen, $C_1$–$C_6$ alkyl, 2-, 3-, or 4-pyridylmethyl, $C_3$–$C_7$, preferably $C_4$–$C_6$, cycloalkyl, $C_1$–$C_6$ alkoxy($C_1$–$C_6$)alkyl, or 2- or 3-tetrahydrofuranyl($C_1$–$C_6$)alkyl. Preferred $C_1$–$C_6$ alkoxy ($C_1$–$C_6$)alkyl groups are 2-methoxyethyl and 2-ethoxyethyl. Preferred tetrahydrofuranyl-($C_1$–$C_6$)alkyl groups are tetrahydrofuran-2-ylmethyl groups. Particularly preferred Z-1 groups are those where one and only one of $R_z$ and $R_y$ is hydrogen.

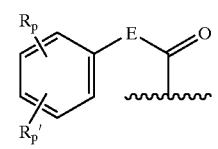

Z-2 where E is a bond or $C_1$–$C_6$ alkylene, each of Rp and $R_p$' are independently hydroxy, halogen, $C_1$–$C_6$ alkyl, or $C_1$–$C_6$ alkoxy. Preferred $R_p$ groups are fluoro, more preferably 4-fluoro, and chloro. Preferred $R_p$' groups are hydrogen, $C_1$–$C_2$ alkoxy, $C_1$–$C_2$ alkyl, fluoro, more preferably 4-fluoro, and chloro. Preferred E groups are a bond and $C_2$ alkylene.

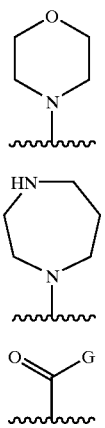

where G is 2-, 3-, or 4-pyridyl, each of which is optionally mono- or disubstituted with $C_1$–$C_6$ alkyl, $C_1$–$C_6$ alkoxy, or halogen.

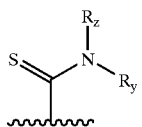

where $R_z$ and $R_y$ are independently hydrogen, $C_1$–$C_6$ alkyl, 2-, 3-, or 4-pyridylmethyl, $C_3$–$C_7$, preferably $C_4$–$C_6$, cycloalkyl, $C_1$–$C_6$ alkoxy($C_1$–$C_6$)alkyl, 2-, or 3-tetrahydrofuranyl($C_1$–$C_6$)alkyl. Preferred $C_1$–$C_6$ alkoxy ($C_1$–$C_6$)alkyl groups are 2-methoxyethyl and 2-ethoxyethyl. Preferred tetrahydrofuranyl($C_1$–$C_6$)alkyl groups are tetrahydrofuran-2-ylmethyl groups. Particularly preferred Z-6 groups are those where one and only one of $R_z$ and $R_y$ is hydrogen.

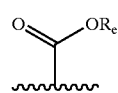

where $R_e$ is hydrogen or $C_1$–$C_6$ alkyl. Preferred Re groups in Z-7 are hydrogen atoms.

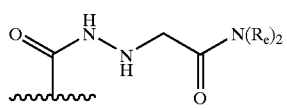

where each $R_e$ is independently hydrogen or $C_1$–$C_6$ alkyl. Preferred $R_e$ groups in Z-8 are hydrogen and methyl.

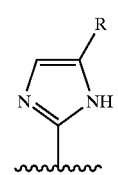

where R is $C_1$–$C_6$ alkyl.

The present invention also encompasses compounds of Formula IV:

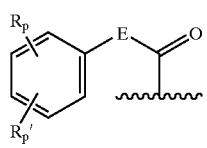

wherein W, X, and Z are as defined above in Formula I; and

A, B, C, and D are independently $CR_1$ or nitrogen, provided that no more than two of A, B, C, and D are nitrogen simultaneously; and $R_1$ is hydrogen, lower alkyl, lower alkoxy, halogen, hydroxy, hydroxyalkyl, aminoalkyl, alkoxyalkyl, thio, or arylalkyl.

Preferred compounds of Formula IV are where W is phenyl or 2-, 3-, or 4-pyridyl each of which is optionally mono or disubstituted independently with halogen, hydroxyl, lower alkyl, or lower alkoxy.

Still other preferred compounds of Formula IV are those where A is nitrogen and B, C, and D are hydrogen.

Preferred Z groups in Formula IV include Z-1, Z-2, Z-3, Z-4, Z-5, Z-6, Z-7, Z-8, and Z-9 groups.

where $R_z$ and $R_y$ are independently hydrogen, $C_1$–$C_6$ alkyl, 2-, 3-, or 4-pyridylmethyl, $C_3$–$C_7$, preferably $C_4$–$C_6$, cycloalkyl, $C_1$–$C_6$ alkoxy($C_1$–$C_6$)alkyl, or 2- or 3-tetrahydrofuranyl($C_1$–$C_6$)alkyl. Preferred $C_1$–$C_6$ alkoxy ($C_1$–$C_6$)alkyl groups are 2-methoxyethyl and 2-ethoxyethyl. Preferred tetrahydrofuranyl-($C_1$–$C_6$)alkyl groups are tetrahydrofuran-2-ylmethyl groups. Particularly preferred Z-1 groups are those where one and only one of $R_z$ and $R_y$ is hydrogen.

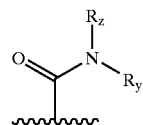

where E is a bond or $C_1$–$C_6$ alkylene, each of Rp and $R_p'$ are independently hydroxy, halogen, $C_1$–$C_6$ alkyl, or $C_1$–$C_6$ alkoxy. Preferred $R_p$ groups are fluoro, more preferably 4-fluoro, and chloro. Preferred $R_p'$ groups are hydrogen, $C_1$–$C_2$ alkoxy, $C_1$–$C_2$ alkyl, fluoro, more preferably 4-fluoro, and chloro. Preferred E groups are a bond and $C_2$ alkylene.

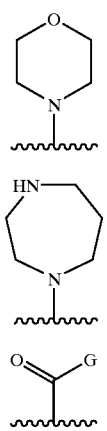

Z-3

Z-4

Z-5 where G is 2-, 3-, or 4-pyridyl, each of which is optionally mono- or disubstituted with $C_1$–$C_6$ alkyl, $C_1$–$C_6$, alkoxy, or halogen.

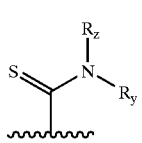

Z-6 where $R_z$ and $R_y$ are independently hydrogen, $C_1$–$C_6$ alkyl, 2-, 3-, or 4-pyridylmethyl, $C_3$–$C_7$, preferably $C_4$–$C_6$, cycloalkyl, $C_1$–$C_6$ alkoxy($C_1$–$C_6$)alkyl, 2-, or 3-tetrahydrofuranyl($C_1$–$C_6$)alkyl. Preferred $C_1$–$C_6$ alkoxy ($C_1$–$C_6$)alkyl groups are 2-methoxyethyl and 2-ethoxyethyl. Preferred tetrahydrofuranyl($C_1$–$C_6$)alkyl groups are tetrahydrofuran-2-ylmethyl groups. Particularly preferred Z-6 groups are those where one and only one of $R_z$ and $R_y$ is hydrogen.

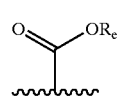

Z-7 where $R_e$ is hydrogen or $C_1$–$C_6$ alkyl. Preferred $R_e$ groups in Z-7 are hydrogen atoms.

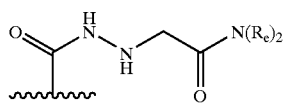

Z-8 where each $R_e$ is independently hydrogen or $C_1$–$C_6$ alkyl. Preferred $R_e$ groups in Z-8 are hydrogen and methyl.

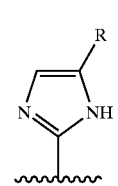

Z-9 where R is $C_1$–$C_6$ alkyl.

Preferred compounds of the invention are encompassed by the following formulae:

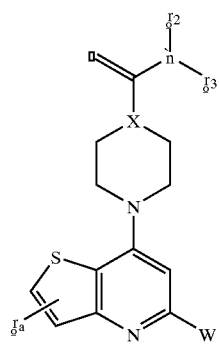

Va

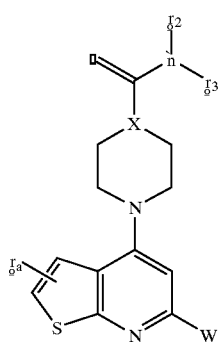

Vb where W, X, and Y are as defined above in Formula I;
$R_a$ is hydrogen, lower alkyl, $C_1$–$C_6$ alkoxy, hydroxy, halogen, amino, mono- or di($C_1$–$C_6$)alkylamino, or trifluoromethyl; and
$R_2$ and $R_3$ are the same or different and represent
hydrogen, lower alkyl, hydroxyalkyl, aminoalkyl, alkoxyalkyl, haloalky, or amidoalkyl;
aryl, arylalkyl, heteroaryl, or heteroarylalkyl each of which may be mono or disubstituted independently on the aryl group with halogen, thio, hydroxyl, lower alkyl, lower alkoxy, or amino; or
a $C_3$–$C_7$ carbocyclic or $C_3$–$C_7$ carbocyclic ($C_1$–$C_6$) alkyl group having from 3–7 members, where up to two of which members are optionally hetero atoms selected from oxygen and nitrogen and where any member of the carbocyclic group is optionally substituted with halogen, lower alkyl or lower alkoxy.

More preferred compounds of Formula Va and Vb are those where $R_2$ is hydrogen and where W is aryl or heteroaryl mono or disubstituted independently with halogen, hydroxyl, lower alkyl, or lower alkoxy.

Other preferred compounds are represented by Formula VI.

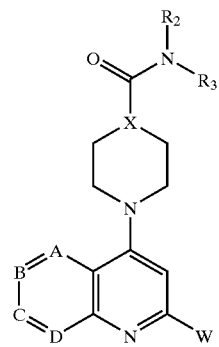

VI where W, and X are as defined above in Formula I and wherein:

A, B, C, and D are independently $CR_1$ or nitrogen, provided that at least one but not more than two of A, B, C, and D are nitrogen simultaneously;

$R_1$ is hydrogen, lower alkyl, lower alkoxy, halogen, hydroxy, hydroxyalkyl, aminoalkyl, alkoxyalkyl, thio, or arylalkyl; and $R_2$ and $R_3$ are the same or different and represent
hydrogen, lower alkyl, hydroxyalkyl, aminoalkyl, alkoxyalkyl, haloalky, or amidoalkyl;
aryl, arylalkyl, heteroaryl, or heteroarylalkyl each of which may be mono or disubstituted independently on the aryl group with halogen, thio, hydroxyl, lower alkyl, lower alkoxy, or amino, or
a carbocyclic or carbocyclic($C_1$–$C_6$)alkyl group having from 3–7 members in the carbocyclic portion, where up to two of which members are optionally hetero atoms selected from oxygen and nitrogen and where any member of the carbocyclic group is optionally substituted with halogen, lower alkyl or lower alkoxy.

More preferred compounds of Formula VI are where W is phenyl or 2-, 3-, or 4-pyridyl each of which is optionally mono or disubstituted independently with halogen, hydroxyl, lower alkyl, or lower alkoxy; where A is nitrogen and B, C, and D are hydrogen; and where $R_2$ is hydrogen and $R_3$ is hydrogen or lower alkyl.

Still other preferred compounds of the invention are represented by Formula VIIa and VIIb.

VIIa

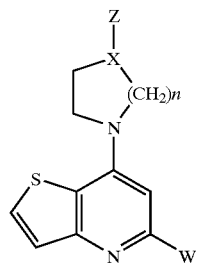

VIIb

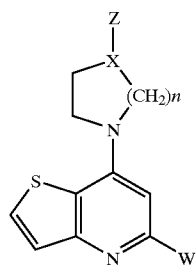

where W and X are as above in Formula I and wherein n is the integer 2 or 3;

Z is an electron pair when X is oxygen;

Z is hydrogen;

Z is aryl optionally substituted with one or two groups selected from lower alkyl, lower alkoxy, or halogen; or

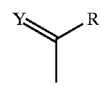

where

Z is
Y oxygen or sulfur;
R is amino, optionally substituted with one or two groups selected from lower alkyl, alkoxyalkyl, aminoalkyl, haloalkyl, hydroxy, aminoalkyl, amidoalkyl, heteroaryl.

More preferred compounds of Formula VIIa and VIIb are where where Y is oxygen and W is aryl or heteroaryl mono or disubstituted independently with halogen, hydroxyl, lower alkyl, or lower alkoxy.

The present invention also encompasses compounds of Formula VIIIa and Formula VIIIb:

VIIIa

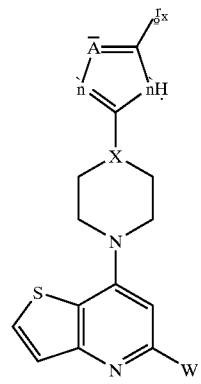

VIIIb

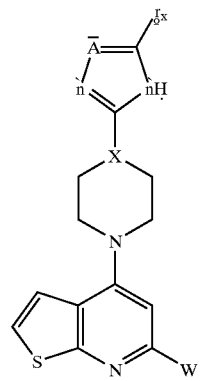

wherein W and X are as defined above for Formula I;

$R_x$ is hydrogen, lower alkyl, $C_1$–$C_6$ alkoxy, hydroxy, halogen, amino, mono- or di($C_1$–$C_6$)alkylamino, or trifluoromethyl;

A is nitrogen or CH; and $R_x$ is hydrogen, lower alkyl, hydroxy, lower alkoxy, hydroxyalkyl, or aminoalkyl, or mono- or di($C_1$–$C_6$) alkylamino ($C_1$–$C_6$)alkyl.

Preferred compounds of Formula VIIIa and VIIIb are where W is phenyl or 2-, 3-, or 4-pyridyl, each of which is optionally mono or disubstituted independently with halogen, hydroxyl, lower alkyl, or lower alkoxy. Other preferred compounds of Formulae VIIIa and b are those where X is CH and A is CH. More preferred compounds of Formula VIIIa and b where A is CH are those where $R_x$ is hydrogen, methyl or ethyl. Particularly preferred compounds of Formulae VIIIa and b where A is CH are those where W is phenyl optionally substituted with one or two groups selected from halogen, preferably fluoro and chloro, methyl, ethyl, or amino.

Still other preferred compounds of Formulae VIIIa and b are those where X is CH and A is nitrogen. More preferred compounds of Formula VIIIa and b where A is nitrogen are those where $R_x$ is hydrogen, methyl or ethyl. Particularly preferred compounds of Formulae VIIIa and b where A is nitrogen are those where W is phenyl optionally substituted with one or two groups selected from halogen, preferably fluoro and chloro, methyl, ethyl, or amino.

By "alkyl" and "lower alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy" and "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentoxy, isopentoxy, neopentoxy, hexoxy, 2-hexoxy, 3-hexoxy, and 3-methylpentoxy.

By the term "halogen" in the present invention is meant fluorine, bromine, chlorine, and iodine. Preferred halogens are fluorine, bromine, and chlorine.

By heteroaryl is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl. Preferred heteroaryl groups are pyrimidinyl, pyridyl, imidazolyl, naphthyridinyl, and benzimidazolyl groups that are optionally substituted as described herein.

The heteroaryl groups of the invention may be substituted with up to four groups selected from, for example, $C_1$–$C_6$ alkyl, hydroxy, $C_1$–$C_6$ alkoxy, hydroxy($C_1$–$C_6$)alkyl, amino ($C_1$–$C_6$)alkyl, mono- or di($C_1$–$C_6$)alkylamino($C_1$–$C_6$)alkyl, halogen, thio, hydroxy, amino, mono- or di($C_1$–$C_6$) alkylamino, $C_3$–$C_7$ cycloalkyl, alkoxy($C_1$–$C_6$)alkyl, halo ($C_1$–$C_6$)alkyl, and amidoalkyl. Other heteroaryl substituents include, for example, phenyl, pyridyl, pyrimidiyl, imidazolyl, morpholinyl, piperidinyl, piperazinyl, pyrrolyl, and pyrrolidinyl.

By 1H-1,4-Diazepine is meant the structure

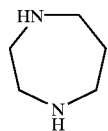

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. Preferred aryl groups are phenyl and napthyl groups that are optionally substituted as described herein.

The aryl groups of the invention may be substituted with up to four groups selected from, for example, $C_1$–$C_6$ alkyl, hydroxy, $C_1$–$C_6$ alkoxy, hydroxy($C_1$–$C_6$)alkyl, amino ($C_1$–$C_6$)alkyl, mono- or di($C_1$–$C_6$)alkylamino($C_1$–$C_6$)alkyl, halogen, thio, hydroxy, amino, mono- or di($C_1$–$C_6$) alkylamino, $C_3$–$C_7$ cycloalkyl, alkoxy($C_1$–$C_6$)alkyl, halo ($C_1$–$C_6$)alkyl, and amidoalkyl. Other aryl substituents include, for example, phenyl, pyridyl, pyrimidiyl, imidazolyl, morpholinyl, piperidinyl, piperazinyl, pyrrolyl, and pyrrolidinyl.

Representative $C_3$–$C_7$ carbocyclic or $C_3$–$C_7$ carbocyclic ($C_1$–$C_6$)alkyl groups that include one or two oxygen or nitrogen atoms are, for example, morpholino, pyrrolo, imidazolyl, piperidinyl, piperazinyl, pyrazinyl, pyranyl, tetrahydropyanyl, pyrrolidinyl, 1H-1,4-diazepinyl, and pyrrolinyl. These groups are optionally substituted with one or two groups, preferably one group, selected from halogen, lower alkyl and lower alkoxy.

Representative compounds of the invention are shown below in Table 1.

TABLE 1

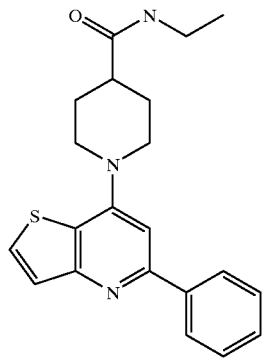

Compound 1

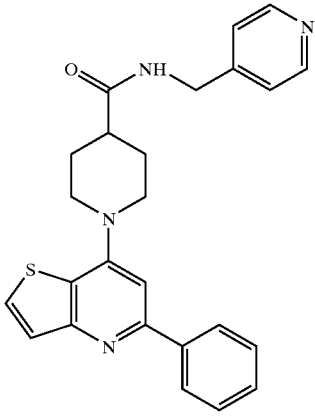

TABLE 1-continued
Compound 5
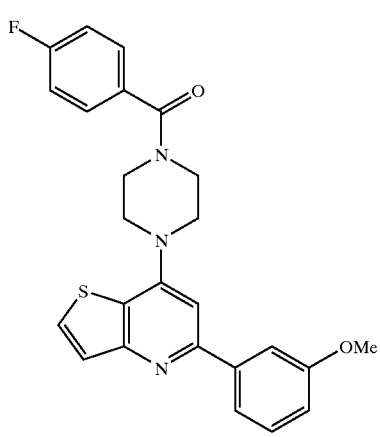
Compound 10
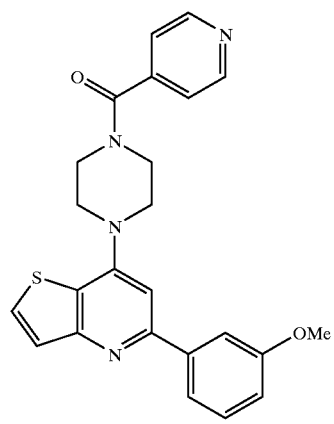
Compound 7
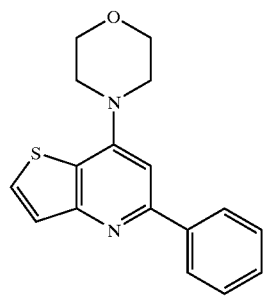
Compound 13
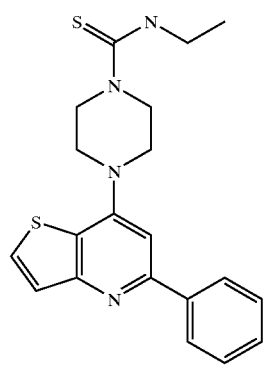
Compound 9
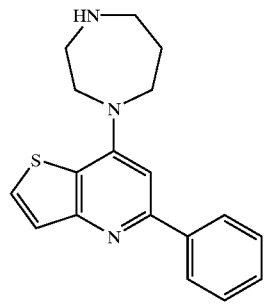
Compound 20
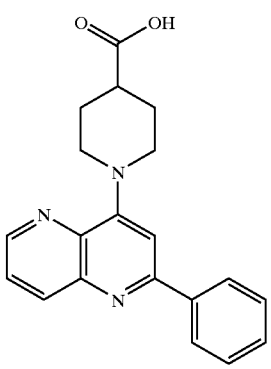

TABLE 1-continued
Compound 21
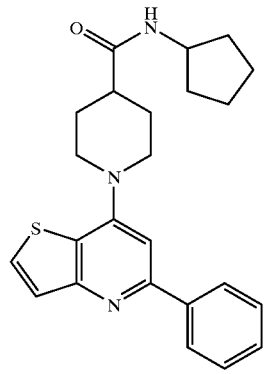
Compound 29
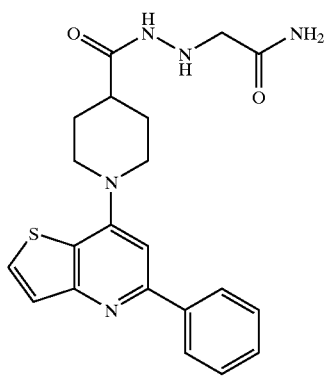
Compound 33
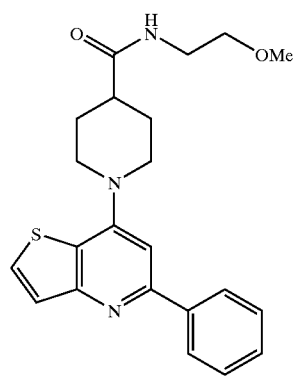
TABLE 1-continued
Compound 35
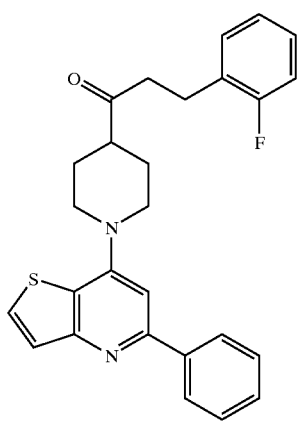
Compound 38
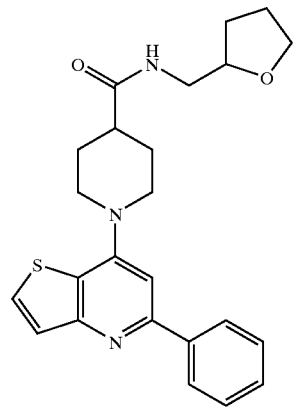
Compound 45
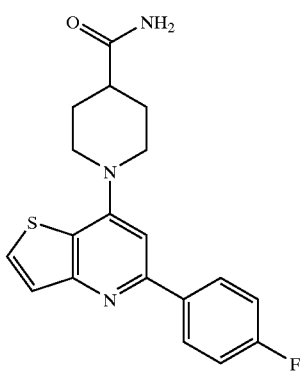

TABLE 1-continued

Compound 52

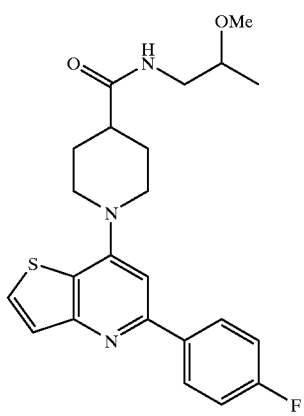

Compound 59

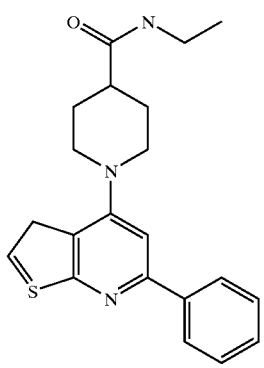

Compound 62

Representative compounds of the present invention, which are encompassed by Formula I, include, but are not limited to the compounds in Table I and their pharmaceutically acceptable acid and base addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC\text{-}(CH_2)_n\text{-}COOH$ where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

The compounds of Formula I and their salts are suitable for the diagnosis and treatment of anxiety, Down Syndrome, sleep, cognitive and seizure disorders, and overdose with benzodiazepine drugs and for enhancement of alertness, both in human and non-human animals and domestic pets, especially dogs and cats and farm animals such as sheep, swine and cattle.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. guch materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It will be convenient to formulate these animal feed and drinking water compositions with a mullet-dose of the drug so that the animal takes in an appropriate quantity of the composition along with its diet. It will also be convenient to present the composition as a premix for addition to the feed or drinking water.

The compounds of the invention may be prepared using the synthetic routes outlined in the following schemes.

Scheme I

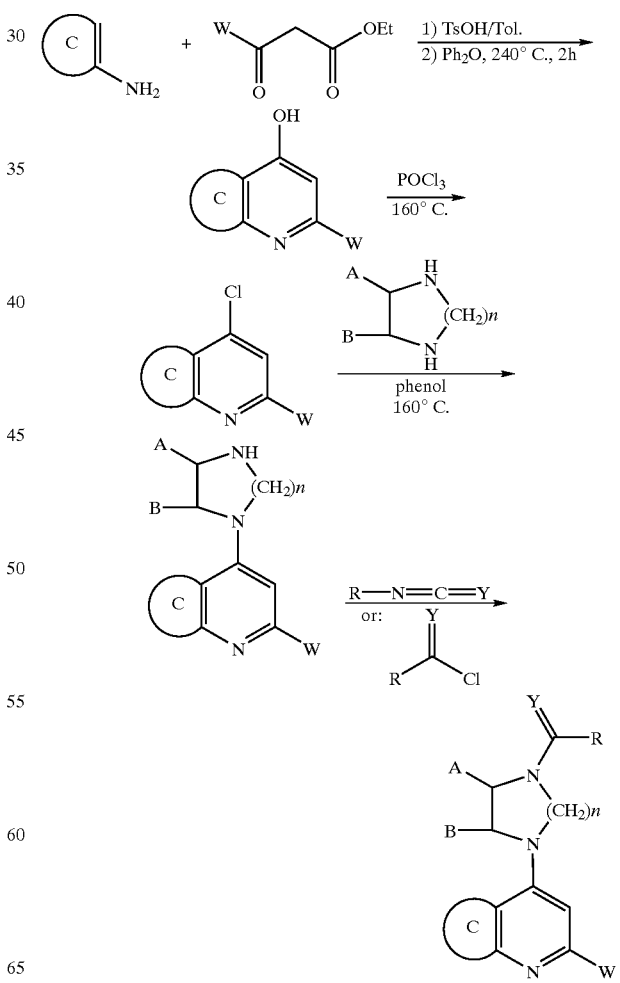

Scheme II
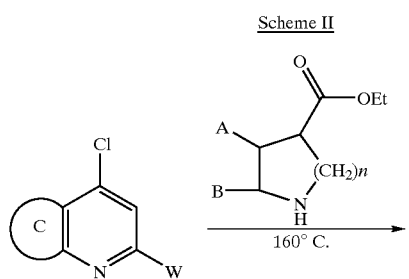
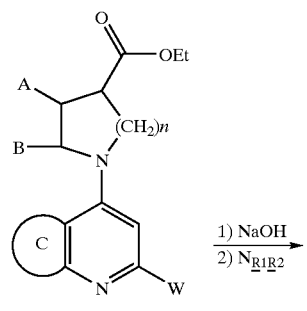
1) NaOH
2) $N_{R_1R_2}$
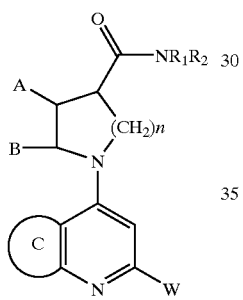
Scheme III
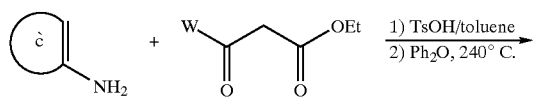
1) TsOH/toluene
2) Ph$_2$O, 240° C.
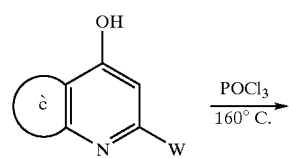
POCl$_3$
160° C.
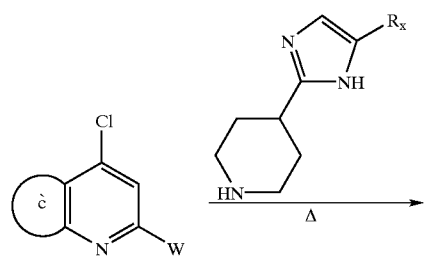
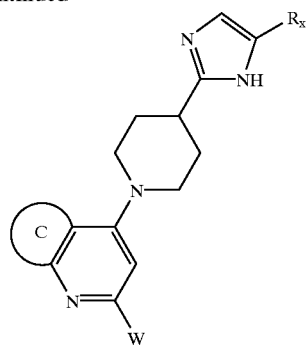
Scheme IV
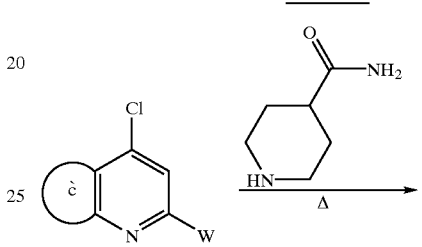
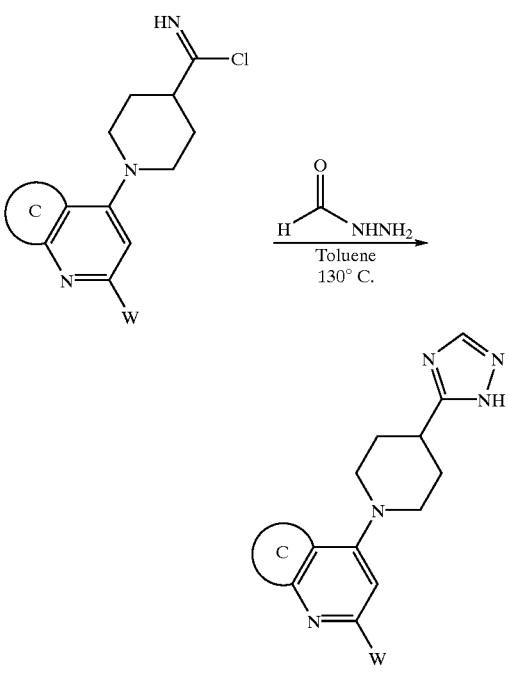

where A, B, the C ring, W, Y, R, $R_2$, $R_3$ and n are as defined above in Formula I.

Those having skill in the art will recognize that the starting materials may be varied and additional steps employed to produce compounds encompassed by the present invention, as demonstrated by the following examples. For example, certain groups, e.g., nitrogen and hydroxy, may require protection during the synthesis.

As shown in Scheme I, an aniline is reacted with a suitable β-keto ester in the presence of an acid, such as, for example, P-toluenesulfonic acid, to form a 4-hydroxypyridine which is subsequently converted to the 4-chloropyridine upon treatment with a nucleophilic halogenating reagent such phosphorus oxychloride. The resulting chloride is reacted with the desired 1,4-diheterocarbocycle, such as a piperazine or 1,4-diazaperhydropine at elevated temperatures to form the N-alkylated product. The piperdine can then be further alkylated with a desired isocyanate or isothiocyanate, such as, for example, methyl isocyanate, to form the target compound.

As shown in Scheme II, a 4-chloropyridine is reacted with a reagent such as ethyl 4-piperdinecarboxylate at elevated temperatures to form the N-alkylated ester. The ester is treated with an amine, such as methylamine, in the presence of a base such as sodium hydroxide to form the resulting amide.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLE 1

1. 5-(4-Fluorophenyl)-thieno[3,2-b]pyridin-7-ol

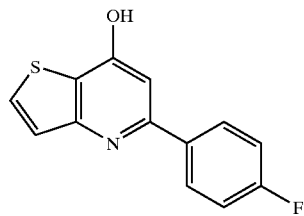

A mixture of 3-amino-2-thiophenecarboxylic acid (8 g, 49 mmol), ethyl 4-fluorobenzoylacetate (9.6 g, 49 mmol), and p-toluenesulfonic acid monohydrate (0.2 g, 1 mmol) in toluene (100 mL) is refluxed for 20 hours with a Dean-Stark water trap to remove produced water. The mixture is cooled to room temperature. The resulting precipitate is filtered and washed with diethyl ether. The solid is dissolved in diphenyl ether (80 mL) and heated at 220° C. for 2 hours. The reaction solution is then cooled to room temperature and diluted with diethyl ether; the precipitate is filtered and washed with diethyl ether to give 5-(4-fluorophenyl)-thieno[3,2-b] pyridin-7-ol (2 g, 17% yield) as brown crystalline needles, m.p. 316–318° C.

2. 7-Chloro-5-(4-fluorophenyl)thieno[3,2-b]pyridine

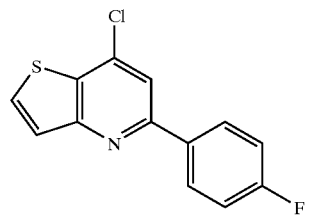

A solution of 5-(4-fluorophenyl)-thieno[3,2-b]pyridin-7-ol (1.6 g) in phosphorus oxychloride (50 mL) is refluxed for 3 hours. After the excess amount of phosphorus oxychloride is removed under vacuum, the residue is treated with ethyl acetate (20 mL) and NaOH (2N, 20 mL). The mixture is then extracted with ethyl acetate (3×20 mL). The combined organic layers are washed with brine and dried over $MgSO_4$. Evaporation of the solvent affords 7-chloro-5-(4-fluorophenyl)thieno[3,2-b]pyridine (1.5 g, 88% yield) as a white solid, m.p. 119–121° C.

3. 1-(5-(4-Fluorophenyl)thieno[3,2-b]pyridin-7-yl)-4-piperidinecarboxamide

A mixture of 7-chloro-5-(4-fluorophenyl)thieno[3,2-b] pyridine (68 mg, 0.26 mmole), isonipecotamide (66 mg, 0.52 mmole), and sodium acetate (21 mg, 0.26) in 1-methyl-2-pyrrolidone (3 mL) is stirred and heated in an oil bath at 160° C. for 4 hours. The reaction mixture is then cooled and diluted with EtAc (15 mL), transferred to a separatory funnel, and washed with water (3×15 mL). The organic layer is dried over sodium sulfate and concentrated. The residue is recrystalized with ethyl acetate to give 1-(5-(4-fluorophenyl)thieno[3,2-b]pyridin-7-yl)-4-piperidinecarboxamide (55 mg, 60% yield) as a white solid. This material is dissolved in ethyl acetate and HCl saturated ethyl acetate (2 mL) is added. The solution is concentrated to afford the HCl salt as a greasy oil. 1-(5-phenylthieno[3,2-b]pyridin-7-yl)-4-piperidinecarboxamide hydrochloride (compound 3) is precipitated out of an ether solution, collected by filtration, washed with ether, and dried in vacuo to afford the final product. m.p. 303–305° C. (dec).

EXAMPLE 2

1. 4-Chloro-6-phenylthieno[2,3-b]pyridine

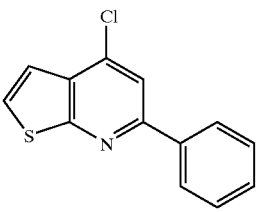

A mixture of 3-aminothiophene (4 g, 0.04 mole), ethyl benzoylacetate (11 mL, 0.06 mole), toluene (100 mL), and p-toluene sulfonic acid monohydrate (300 mg) is stirred and heated under reflux with a Dean-Stark water trap at 120° C. for 16 hours. The reaction mixture is concentrated, and diphenyl ether (30 mL) is added. After heating at 240° C. for 1 hour, the reaction mixture was allowed to cool to room temperature. The reaction mixture is diluted with hexane, and the semi-solid collected is then purified by short silica gel column (CH$_2$Cl$_2$/MeOH/NH$_4$OH: 10:1:0.1). The resulting product, 4-hydroxy-6-phenyl-thieno[2,3-b]pyridine, is treated with phosphorus oxychloride (30 mL) and heated under reflux for 3 hours. This mixture is cooled to room temperature, poured over ice, neutralized with 10 N sodium hydyoxide, and extracted with methylene chloride (3×20 mL). The combined organic layers are dried over sodium sulfate and concentrated in vacuo. The residue is purified by chromatography to give 4-chloro-6-phenylthieno[2,3-b] pyridine as a yellowish solid (1.1 g, 11% total yield), m.p. 83–85° C.

2. Ethyl 1-(6-Phenylthieno[2,3-b]pyridin-4-yl)-4-piperidinecarboxylate

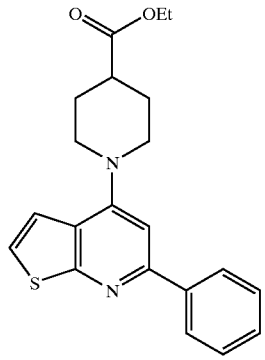

A mixture of 4-chloro-6-phenyl-thieno[2,3-b]pyridine (200 mg, 0.82 mmole) and ethyl isonipecotate (5 mL) is stirred and heated in an oil bath at 170° C. for 6 hours. The reaction mixture is cooled and purified on a preparative tlc plate to give ethyl 1-(6-phenylthieno[2,3-b]pyridin-4-yl)-4-piperidinecarboxylate (100 mg, 33% yield) as a colorless oil.

EXAMPLE 3

N-Ethyl 1-(5-phenylthieno[3,2-b]pyridin-7-yl)-4-piperidinecarboxamide

A solution of 1-(5-phenylthieno[3,2-b]pyridin-7-yl)-4-piperidinecarboxylic acid ethyl ester (50 mg, 0.14 mmole), ethylamine (2 mL), and a catalytic amount of sodium cynide in MeOH (10 mL) is heated in a sealed tube at 70° C. oil bath for 48 hours. The solvent is removed on rotary-evaporator. The resulting residue is purified on a preparative tlc plate to give N-Ethyl 1-(5-phenylthieno[3,2-b]pyridin-7-yl)-4 piperidinecarboxamide (20 mg, 39% yield) as a colorless oil. This material is dissolved in ethyl acetate (1 mL), diluted with HCl saturated ethyl acetate (2 mL), and concentrated to afford N-ethyl 1-(6-phenylthieno[2,3-b]pyridin-4-yl)-4-piperidinecarboxamide hydrochloride (compound 1, 26 mg) as greasy oil. The salt is solidified with ether, collected by filtration, washed with ether, and dried in vacuo. m.p. >270° C. (dec).

EXAMPLE 4

1. 1-(5-Phenylthieno[3,2-b]pyridin-7-yl)-4-piperazine

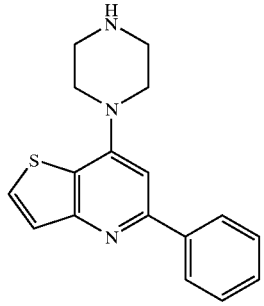

A reaction mixture of 7-chloro-5-phenylthieno[3,2-b] pyridine (200 mg, 0.82 mmole), piperazine (100 mg, 1.19 mmole) and phenol (1 g) is heated under N$_2$ at 160° C. oil bath for 3 hours. The mixture is cooled down to room temperature, dilutied with EtAc (15 mL), transferred to a separatory funnel, and extracted with 5% HCl solution (3×15 mL). The combined acidic extracts are basified using concentrated NH$_4$OH solution and then extracted with CH$_2$Cl$_2$ (3×15 mL). The combined organic layers are dried over soduim sulfate and concentrated, and the crude residue is purified on a preparative tlc plate to give 1-(5-Phenylthieno[3,2-b]pyridin-7-yl)-4-piperazine (90 mg, 37% yield) as a yellowish oil.

2. N-Methyl 1-(5-phenylthieno[3,2-b]pyridin-7-yl)-4-piperazinecarboxamide

A reaction solution of 1-(5-phenylthieno[3,2-b]pyridin-7-yl)-4-piperazine (120 mg, 0.41 mmole) and methyl isocynate (0.5 mL) in toluene (10 mL) is heated in a 120° C. oil bath for 1 hour. The resulting solution is cooled down to room temperature and concentrated. The crude residue is purified on a preparative tlc plate to give N-Methyl 1-(5-phenylthieno[3,2-b]pyridin-7-yl)-4-piperazinecarboxamide (100 mg, 69% yield) as a colorless oil. This material is dissolved in 1 mL ethyl acetate. Ethyl acetate saturated with HCl (2 mL) is added and the solution is then concentrated to afford 105 mg of N-methyl 1-(5-phenylthieno[3,2-b] pyridin-7-yl)-4-piperazinecarboxamide hydrochloride (compound 2) as a greasy oil. The salt is solidified with ether, collected by filtration, washed with ether, and dried in vacuo. m.p. 185–190° C.

EXAMPLE 5

7-Chloro-5-(4-fluorophenyl)thieno[3,2-b]pyridine

A solution of 5-(4-fluorophenyl)-thieno[3,2-b]pyridin-7-ol (1.6 g) in phosphorus oxychloride (50 mL) is refluxed for 3 hours. After the excess phosphorus oxychloride is removed under vacuum, the residue is treated with ethyl acetate (20 mL), and NaOH (2N, 20 mL). The mixture is extracted with ethyl acetate (3×20 mL) and the combined organic layers are washed with brine and dried over MgSO$_4$. Evaporation of the solvent gives 7-chloro-5-(4-fluorophenyl)thieno[3,2-b]pyridine (1.5 g, 88% yield) as a white solid, m.p. 119–121° C.

EXAMPLE 6

5-(4-Fluorophenyl)-7-[4-(1H-imidazol-2-yl)-1-piperidinyl thieno[3,2-b]pyridine A mixture of 7-chloro-5-(4-fluorophenyl)thieno[3,2-b] pyridine (146 mg, 0.53 mmole), 4-(1H-imidazol-2-yl)

piperidine hydrochloride (See U.S. Pat. No. 4,431,653) (100 mg, 0.53 mmole) and sodium acetate (50 mg) in ethylene glycol (10 mL) is stirred and heated at 160° C. for 16 hours. It is then cooled, diluted with ethylacetate (15 mL), and washed with water (3×15 mL). The organic layer is dried over sodium sulfate, and concentrated. The residue is purified by preparative tlc plate to give 5-(4-fluorophenyl)-7-[4-(1H-imidazol-2-yl)-1-piperidinyl thieno[3,2-b]pyridine (36 mg, 18% yield) as a white solid, m.p. 95° C. (compound 63).

EXAMPLE 7

1-(5-(4-Fluorophenyl)thieno[3,2-b]pyridin-7-yl) piperidine-4-carboxamide

A mixture of 7-chloro-5-(4-fluorophenyl)thieno[3,2-b] pyridine (68 mg, 0.26 mmole), isonipecotamide (66 mg, 0.52 mmole), and sodium acetate (21 mg, 0.26 mmole) in 1-methyl-2-pyrrolidone (3 mL) is stirred and heated in an oil bath at 160° C. for 4 hours. The mixture is then cooled, diluted with ethyl acetate (15 mL), and washed with water (3×15 mL). The organic layer is dried over sodium sulfate, and concentrated. The residue is recrystalized from ethyl acetate to give 1-(5-(4-fluorophenyl)thieno[3,2-b]pyridin-7-yl)piperidine-4-carboxamide (Compound 64, 55 mg, 60% yield) as a white solid product (m.p. 251° C.–253° C.).

EXAMPLE 8

5-(4-Fluorophenyl)-7-[4-(1H-1,2,4-triazol-3-yl)-1-piperidinyl]thieno[3,2-b]pyridine A suspension of 1-(5-(4-fluorophenyl)thieno[3,2-b] pyridin-7-yl)piperidine-4-carboxamide (100 mg, 0.32 mmole) in phosphorus oxochloride (5 mL) is refluxed for 0.5 hours. After the excess phosphorus oxychloride is removed under vacuum, the residue is treated with ethyl acetate (5 mL), and ice-water (10 mL). The resulting mixture is subsequently extracted with ethyl acetate (3×10 mL) and the combined organic layers are washed with brine, dried over sodium sulfate, and concentrated. The residue is then dissolved in toluene (5 mL), then formic hydrazid (100 mg, 1.7 mmole), and formic acid (0.05 mL) are added. The reaction mixture is refluxed for 16 hours, cooled, diluted with ethyl acetate (15 mL), and washed with water (3×15 mL). The organic layer is dried over sodium sulfate, and concentrated.

The residue is purified by preparative tlc plate to give 5-(4-fluorophenyl)-7-[4-(1H-1,2,4-triazol-3-yl)-1-piperidinyl]thieno[3,2-b]pyridine (7 mg, 6% yield) as a white solid. This material is dissolved in ethyl acetate (1 mL), saturated with HCl (2 mL), and then concentrated to afford 5-(4-fluorophenyl)-7-[4-(1H-1,2,4-triazol-3-yl)-1-piperidinyl]thieno[3,2-b]pyridine hydrochloride (compound 65) as greasy oil.

The salt is solidified with ether, collected by filtration, washed with ether and dried in vacuo, m.p. >300° C. (dec).

EXAMPLE 9

The following compounds were prepared essentially according to the procedures set forth in Examples 1–8:

j) 4-Pyridinylcarbonyl-1-(5-(3-methoxyphenyl)thieno[3,2-b]pyridin-7-yl))-4-piperazine hydrochloride (compound 13), m.p. 215–217° C.

k) N-Ethyl 1-(5-(3-methoxyphenyl)thieno[3,2-b]pyridin-7-yl)-4-piperazinecarboxamide hydrochloride (compound 14), m.p. >198–201° C.

l) N-n-Propyl 1-(5-(4-fulorophenyl)thieno[3,2-b]pyridin-7-yl)-4-piperazinecarboxamide hydrochloride (compound 15), m.p. >130° C. (dec).

m) N-i-Propyl 1-(5-(4-fulorophenyl)thieno[3,2-b]pyridin-7-yl)-4-piperazinecarboxamide hydrochloride (compound 16), m.p. 127–129° C. (dec).

n) N-n-Butyl 1-(5-(4-fulorophenyl)thieno[3,2-b]pyridin-7-yl)-4-piperazinecarboxamide hydrochloride (compound 17), m.p. >93° C. (dec).

o) N-(3-Chloro-n-Propyl) 1-(5-(4-fluorophenyl)thieno[3,2-b]pyridin-7-yl)-4-piperazinecarboxamide hydrochloride (compound 18), m.p. 235–238° C. (dec).

p) N-Ethyl 1-(5-(4-fluorophenyl)thieno[3,2-b]pyridin-7-yl)-4-piperazinecarboxamide hydrochloride (compound 19), m.p. >147° C. (dec).

q) N-Ethyl 1-(5-phenylthieno[3,2-b]pyridin-7-yl)-4-piperazinecarbothioamide hydrochloride (compound 20), m.p. >° C. (dec).

a) 1-(5-(2-Fluorophenyl)thieno[3,2-b]pyridin-7-yl)-4-piperidinecarboxamide (compound 4), m.p. 194–195° C.

b) N-4-Picolyl-1-(5-phenylthieno[3,2-b]pyridin-7-yl)-4-piperidinecarboxamide dihydrochloride (compound 5), m.p. 176–178° C. (dec).

c) N-(2-Hydroxyethyl) 1-(5-phenylthieno[3,2-b]pyridin-7-yl)-4-piperidinecarboxamide hydrochloride (compound 6), m.p. >220° C. (dec).

d) 4-Fluorophenylcarbonyl-1-(5-(3-methoxyphenyl)thieno[3,2-b]pyridin-7-yl))-4-piperazine hydrochloride (compound 7), m.p. >174° C. (dec).

e) N-Methylhexahydro- 4-(5-phenylthieno[3,2-b]pyridin-7-yl)-(1H-1,4-diazepine) (compound 8), m.p. >220° C. (dec).

f) 4-(5-Phenylthieno[3,2-b]pyridin-7-yl)morpholine hydrochloride (compound 9), m.p. 195–198° C.

g) 1-(5-Phenylthieno[3,2-b]pyridin-7-yl)-[1H-1,4-diazepine] dihydrochloride (compound 10), m.p. >255° C. (dec).

h) N-Ethylhexahydro-4-(5-phenylthieno[3,2-b]pyridin-7-yl)-(1H-1,4-diazepine)-1-carboxamide dihydrochloride (compound 11), m.p. >180° C. (dec).

i) N-Ethyl 1-(5-phenylthieno[3,2-b]pyridin-7-yl)-4-piperazinecarboxamide hydrochloride (compound 12), m.p. >240° C. (dec).

r) 1-(2-Phenyl-1,5-naphthyridin-4-yl)-4-piperidinecarboxylic acid ethyl ester hydrochloride (compound 21), m.p. >180° C. (dec).

s) N-Ethyl 1-(2-phenyl-1,5-naphthyridin-4-yl)-4-piperidinecarboxamide hydrochloride (compound 22), m.p. >210° C. (dec).

t) N-Methyl 1-(5-phenylthieno[3,2-b]pyridin-7-yl)-4-piperidinecarboxamide hydrochloride (compound 23), m.p. >260° C. (dec).

u) N-Propyl 1-(5-phenylthieno[3,2-b]pyridin-7-yl)-4-piperidinecarboxamide hydrochloride (compound 24), m.p. 159–160° C. (dec).

v) 1-(5-Phenylthieno[3,2-b]pyridin-7-yl)-4-piperidinecarboxamide hydrochloride (compound 25), m.p. ° C. (dec).

w) N-t-Butyl 1-(5-phenylthieno[3,2-b]pyridin-7-yl)-4-piperidinecarboxamide hydrochloride (compound 26), m.p. 270–272° C. (dec).

x) N-n-Butyl 1-(5-phenylthieno[3,2-b]pyridin-7-yl)-4-piperidinecarboxamide hydrochloride (compound 27), m.p. 170–172° C. (dec).

y) N-Cyclopropyl 1-(5-phenylthieno[3,2-b]pyridin-7-yl)-4-piperidinecarboxamide hydrochloride (compound 28), m.p. 199–201° C. (dec).

z) N-Cyclopentyl 1-(5-phenylthieno[3,2-b]pyridin-7-yl)-4-piperidinecarboxamide hydrochloride (compound 29), m.p. 179–181° C. (dec).

aa) N-(2-Aminoethyl) 1-(5-phenylthieno[3,2-b]pyridin-7-yl)-4-piperidinecarboxamide hydrochloride (compound 30), m.p. 176–178° C. (dec).

bb) N-(2-Ethylaminoethyl) 1-(5-phenylthieno[3,2-b]pyridin-7-yl)-4-piperidinecarboxamide hydrochloride (compound 31), m.p. >95° C. (dec).

cc) N-(2-Dimethylaminoethyl) 1-(5-phenylthieno[3,2-b]pyridin-7-yl)-4-piperidinecarboxamide hydrochloride (compound 32), m.p. >150° C. (dec).

dd) N-Glycinamidyl 1-(5-phenylthieno[3,2-b]pyridin-7-yl)-4-piperidinecarboxamide hydrochloride (compound 33), m.p. 158–160° C. (dec).

ee) N-(2-Hydroxyethyl) 1-(5-phenylthieno[3,2-b]pyridin-7-yl)-4-piperidinecarboxamide hydrochloride (compound 34), m.p. >220° C. (dec).

ff) N-(2-Methoxyethyl) 1-(5-phenylthieno[3,2-b]pyridin-7-yl)-4-piperidinecarboxamide hydrochloride (compound 35), m.p. 157–160° C. (dec).

gg) N-(3-Methoxypropyl) 1-(5-phenylthieno[3,2-b]pyridin-7-yl)-4-piperidinecarboxamide hydrochloride (compound 36), m.p. 147–149° C. (dec).

hh) N-Benzyl 1-(5-phenylthieno[3,2-b]pyridin-7-yl)-4-piperidinecarboxamide hydrochloride (compound 37), m.p. 163–165° C. (dec).

ii) N-2-Fluorobenzyl 1-(5-phenylthieno[3,2-b]pyridin-7-yl)-4-piperidinecarboxamide hydrochloride (compound 38), m.p. 164–166° C. (dec).

jj) N-3-Fluorobenzyl 1-(5-phenylthieno[3,2-b]pyridin-7-yl)-4-piperidinecarboxamide hydrochloride (compound 39), m.p. 236–238° C. (dec).

kk) N-4-Fluorobenzyl 1-(5-phenylthieno[3,2-b]pyridin-7-yl)-4-piperidinecarboxamide hydrochloride (compound 40), m.p. 190–192° C. (dec).

ll) N-4-Methylbenzyl 1-(5-phenylthieno[3,2-b]pyridin-7-yl)-4-piperidinecarboxamide hydrochloride (compound 41), m.p. 177–178° C. (dec).

mm) N-4-Ethoxybenzyl 1-(5-phenylthieno[3,2-b]pyridin-7-yl)-4-piperidinecarboxamide hydrochloride (compound 42), m.p. >° C. (dec).

nn) N-4-Pyridylmethyl 1-(5-phenylthieno[3,2-b]pyridin-7-yl)-4-piperidinecarboxamide hydrochloride (compound 43), m.p. >° C. (dec).

oo) N-2-Thiophenylmethyl 1-(5-phenylthieno[3,2-b]pyridin-7-yl)-4-piperidinecarboxamide hydrochloride (compound 44), m.p. >230° C. (dec).

pp) N-2-Tetrahydrofuranylmethyl 1-(5-phenylthieno[3,2-b]pyridin-7-yl)-4-piperidinecarboxamide hydrochloride (compound 45), m.p. >210° C. (dec).

qq) 1-(5-Phenylthieno[3,2-b]pyridin-7-yl)-4-piperidinecarboxylic acid ethyl ester hydrochloride (compound 46), m.p. >° C. (dec).

rr) 1-(5-Phenylthieno[3,2-b]pyridin-7-yl)-4-piperidinecarboxylic acid hydrochloride (compound 47), m.p. >° C. (dec).

ss) 1-(5-(3-Methoxyphenyl)thieno[3,2-b]pyridin-7-yl)-4-piperidinecarboxamide hydrochloride (compound 48), m.p. 133–135° C. (dec).

tt) N-Ethyl 1-(5-(3-methoxyphenyl)thieno[3,2-b]pyridin-7-yl)-4-piperidinecarboxamide hydrochloride (compound 49), m.p. >230° C. (dec).

uu) 1-(5-(4-Ethoxyphenyl)thieno[3,2-b]pyridin-7-yl)-4-piperidinecarboxamide hydrochloride (compound 50), m.p. 211–213° C. (dec).

vv) N-2-Pyridinylmethyl 1-(5-(4-ethoxyphenyl)thieno[3,2-b]pyridin-7-yl)-4-piperidinecarboxamide hydrochloride (compound 51), m.p. 178–180° C. (dec).

ww) 1-(5-(4-Fluorophenyl)thieno[3,2-b]pyridin-7-yl)-4-piperidinecarboxamide hydrochloride (compound 52), m.p. >303° C. (dec).

xx) N-Methyl 1-(5-(4-fluorophenyl)thieno[3,2-b]pyridin-7-yl)-4-piperidinecarboxamide hydrochloride (compound 53), m.p. >° C. (dec).

yy) N-Ethyl 1-(5-(4-fluorophenyl)thieno[3,2-b]pyridin-7-yl)-4-piperidinecarboxamide hydrochloride (compound 54), m.p. 220–222° C. (dec).

zz) N-Propyl 1-(5-(4-fluorophenyl)thieno[3,2-b]pyridin-7-yl)-4-piperidinecarboxamide hydrochloride (compound 55), m.p. 207–209° C. (dec).

aaa) N-(2-Aminoethyl) 1-(5-(4-fluorophenyl)thieno[3,2-b]pyridin-7-yl)-4-piperidinecarboxamide hydrochloride (compound 56), m.p. 115–118° C. (dec).

bbb) N-(2-Dimethylaminoethyl) 1-(5-(4-fluorophenyl)thieno[3,2-b]pyridin-7-yl)-4-piperidinecarboxamide hydrochloride (compound 57), m.p. 180–182° C. (dec).

ccc) N-(2-Hydroxyethyl) 1-(5-(4-fluorophenyl)thieno[3,2-b]pyridin-7-yl)-4-piperidinecarboxamide hydrochloride (compound 58), m.p. 198–200° C. (dec).

ddd) N-(2-Methyoxypropyl) 1-(5-(4-fluorophenyl)thieno[3,2-b]pyridin-7-yl)-4-piperidinecarboxamide hydrochloride (compound 59), m.p. 179–180° C. (dec).

fff) N-Ethyl 1-(5-(4-pyridyl)thieno[3,2-b]pyridin-7-yl)-4-piperidinecarboxamide hydrochloride (compound 60), m.p. >227° C. (dec).

ggg) 1-(6-Phenylthieno[2,3-b]pyridin-4-yl)-4-piperidinecarboxylic acid methyl ester hydrochloride (compound 61), m.p. >220° C. (dec).

hhh) N-Ethyl 1-(6-Phenylthieno[2,3-b]pyridin-4-yl)-4-piperidinecarboxamide hydrochloride (compound 62), m.p. >270° C. (dec).

EXAMPLE 10

The pharmaceutical utility of compounds of this invention are indicated by the following assay for GABAa receptor binding activity.

Assays are carried out as described in Thomas and Tallman (*J. Bio. Chem.* 156: 9838–9842, *J. Neurosci.* 3: 433–440, 1983). Rat cortical tissue is dissected and homogenized in 25 volumes (w/v) of 0.05 M Tris HCl buffer (pH 7.4 at 4° C.). The tissue homogenate is centrifuged in the cold (4°) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05 M Tris HCl buffer (pH 7.4 at 40° C.).

Incubations contain 100 ml of tissue homogenate, 100 ml of radioligand 0.5 nM ($^3$H-RO15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05 M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total−Nonspecific. In some cases, the amounts of unlabeled drugs is varied and total displacement curves of binding are carried out. Data are converted to $IC_{50}$ or $K_i$. The Ki of the compounds in this invention are less than 1 μM.

EXAMPLE 11

In addition, the following assay may be used to determine if the compounds of the invention are agonists, antagonists, or inverse agonists, and, therefore, their specific pharmaceutical utility. The following assay can be employed to determine specific GABAa receptor activity.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Xenopus Laevis oocytes are enzymatically isolated and injected with non-polyadenylated cRNA mixed in a ratio of 4:1:4 for human derived α, β, and γ subunits, respectively. For each subunit combination, sufficient message is injected to result in current amplitudes of >10 nA when 1 μM GABA is applied.

Electrophysiological recordings are carried out using the two electrode voltage-clamp technique at a membrane holding potential of −70 mV.

Compounds are evaluated against a GABA concentration that evokes <10% of the maximal evokable GABA current. Each oocyte is exposed to increasing concentrations of compound in order to evaluate a concentration/effect relationship. Compound efficacy is expressed as a percent-change in current amplitude: 100*((Ic/I)−1), where Ic is the GABA evoked current amplitude observed in the presence of compound and I is the GABA evoked current amplitude observed in the absence of compound.

Specificity of a compound for the Ro15-1788 site is determined following completion of the concentration/effect curve. After washing the oocyte sufficiently to remove previously applied compound, the oocyte is exposed to GABA +1 μM Ro15-1788, followed by exposure to GABA +1 AM Ro15-1788+compound. Percent change due to addition of compound is calculated as described above. Any percent change observed in the presence of Ro15-1788 is subtracted from the percent changes in current amplitude observed in the absence of 1 μM Ro15-1788. These net values are used for the calculation of average efficacy and $EC_{50}$ values.

To evaluate average efficacy and $EC_{50}$ values, the concentration/effect data are averaged across cells and fit to the logistic equation. Average values are reported as mean±standard error.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound or pharmaceutically acceptable salt of the formula:

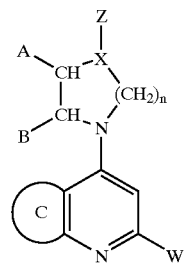

wherein:
n is 0 or an integer of from 1–3;
X is CH, nitrogen, or oxygen;
Z is an electron pair when X is oxygen;
Z is hydrogen, provided that when X is CH, Z is not hydrogen;
Z is aryl, which is unsubstituted or substituted with one or two groups independently selected from lower alkyl, lower alkoxy, or halogen; or

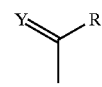

where
Z is
Y is oxygen or sulfur;
R is lower alkyl, hydroxy, lower alkoxy, hydroxyalkyl, or aminoalkyl;
R is aryl or heteroaryl, each of which is mono or disubstituted independently with halogen, thio, hydroxyl, lower alkyl, lower alkoxy, or amino;
R is amino which is unsubstituted or substituted with one or two groups independently selected from
  lower alkyl, hydroxyalkyl, alkoxyalkyl, aminoalkyl, haloalkyl, hydroxy, aminoalkyl, or amidoalkyl;
  heteroaryl, arylalkyl or heteroarylalkyl, each of which is unsubstituted or substituted with one or two groups independently selected from halogen, thio, hydroxyl, lower alkyl, lower alkoxy, or amino; or
  a carbocyclic group having from 3–7 member atoms, where up to two of which atoms are heteroatoms selected from oxygen and nitrogen and where any member of the carbocyclic group is unsubstituted or substituted with halogen, lower alkyl or lower alkoxy; or
R is a carbocyclic group having from 3–7 member atoms, where up to three of which members are heteroatoms selected from oxygen and nitrogen and where any member of the carbocyclic group is unsubstituted or substituted with halogen, lower alkyl, or lower alkoxy;
A and B are the same or different and represent hydrogen, or lower alkyl; and
the C ring represents a thiophene, pyridine, or pyrimidine ring.

2. A pharmaceutical composition comprising a compound of the formula:

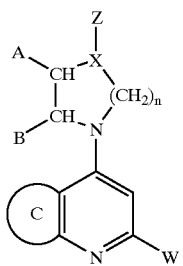

or a pharmaceutically acceptable salt thereof, with at least one carrier, adjuvant or vehicle, wherein:
n is 0 or an integer of from 1–3;
X is CH, nitrogen, or oxygen;
Z is an electron pair when X is oxygen;
Z is hydrogen, provided that when X is CH, Z is not hydrogen;
Z is aryl or heteroaryl, each of which is unsubstituted or substituted with one or two groups independently selected from lower alkyl, lower alkoxy, or halogen; or

where
Z is
  Y is oxygen or sulfur;
  R is lower alkyl, hydroxy, lower alkoxy, hydroxyalkyl, or aminoalkyl;
  R is aryl or heteroaryl, each of which is mono or disubstituted independently with halogen, thio, hydroxyl, lower alkyl, lower alkoxy, or amino;
  R is amino which is unsubstituted or substituted with one or two groups independently selected from
    lower alkyl, hydroxyalkyl, alkoxyalkyl, aminoalkyl, haloalkyl, hydroxy, aminoalkyl, or amidoalkyl;
    heteroaryl, arylalkyl or heteroarylalkyl, each of which is unsubstituted or substituted with one or two groups independently selected from halogen, thio, hydroxyl, lower alkyl, lower alkoxy, or amino; or
    a carbocyclic group having from 3–7 member atoms, where up to two of which atoms are heteroatoms selected from oxygen and nitrogen and where any member of the carbocyclic group is unsubstituted or substituted with halogen, lower alkyl or lower alkoxy; or
  R is a carbocyclic group having from 3–7 member atoms, where up to three of which members are heteroatoms selected from oxygen and nitrogen and where any member of the carbocyclic group is unsubstituted or substituted with halogen, lower alkyl, or lower alkoxy;
A and B are the same or different and represent hydrogen, or lower alkyl;
the C ring represents a thiophene, pyridine, or pyrimidine ring; and
W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl.

3. A pharmaceutical composition according to claim 2 comprising a compound of the formula:

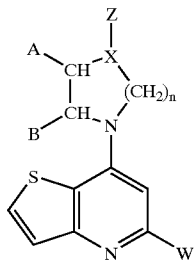

or a pharmaceutically acceptable salt thereof, with at least one carrier, adjuvant or vehicle, wherein:
n is 0 or an integer of from 1–3;
X is CH, nitrogen, or oxygen;
Z is an electron pair when X is oxygen;
Z is hydrogen, provided that when X is CH, Z is not hydrogen;
Z is aryl which is unsubstituted or substituted with one or two groups independently selected from lower alkyl, lower alkoxy, or halogen; or

where
Z is
  Y is oxygen or sulfur;
  R is lower alkyl, hydroxy, lower alkoxy, hydroxyalkyl, or aminoalkyl;
  R is aryl or heteroaryl, each of which is mono or disubstituted independently with halogen, thio, hydroxyl, lower alkyl, lower alkoxy, or amino;
  R is amino, which is unsubstituted or substituted with one or two groups independently selected from
    lower alkyl, hydroxyalkyl, alkoxyalkyl, aminoalkyl, haloalkyl, hydroxy, aminoalkyl, or amidoalkyl;
    heteroaryl, arylalkyl or heteroarylalkyl, each of which is unsubstituted or substituted with one or two groups independently selected from halogen, thio, hydroxyl, lower alkyl, lower alkoxy, or amino; or
    a carbocyclic group having from 3–7 members, where up to two of which members are heteroatoms selected from oxygen and nitrogen and where any member of the carbocyclic group is unsubstituted or substituted with halogen, lower alkyl or lower alkoxy; or
  R is a carbocyclic group having from 3–7 members, where up to three of which members are heteroatoms selected from oxygen and nitrogen and where any member of the carbocyclic group is unsubstituted or substituted with halogen, lower alkyl, or lower alkoxy;
A and B are the same or different and represent hydrogen, or lower alkyl; and
W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl.

4. A pharmaceutical composition according to claim 2 comprising a compound of the formula:

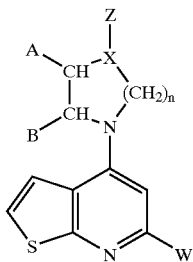

or a pharmaceutically acceptable salt thereof, with at least one carrier, adjuvant or vehicle, wherein:
n is 0 or an integer of from 1–3;
X is CH, nitrogen, or oxygen;
Z is an electron pair when X is oxygen;
Z is hydrogen, provided that when X is CH, Z is not hydrogen;
Z is aryl, which is unsubstituted or substituted with one or two groups independently selected from lower alkyl, lower alkoxy, or halogen; or

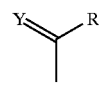

where
Z is
Y is oxygen or sulfur;
R is lower alkyl, hydroxy, lower alkoxy, hydroxyalkyl, or aminoalkyl;
R is aryl or heteroaryl, each of which is mono or disubstituted independently with halogen, thio, hydroxyl, lower alkyl, lower alkoxy, or amino;
R is amino, which is unsubstituted or substituted with one or two groups independently selected from
lower alkyl, hydroxyalkyl, alkoxyalkyl, aminoalkyl, haloalkyl, hydroxy, aminoalkyl, or amidoalkyl;
heteroaryl, arylalkyl or heteroarylalkyl, each of which is unsubstituted or substituted with one or two groups independently selected from halogen, thio, hydroxyl, lower alkyl, lower alkoxy, or amino; or
a carbocyclic group having from 3–7 members, where up to two of which members are heteroatoms selected from oxygen and nitrogen and where any member of the carbocyclic group is unsubstituted or substituted with halogen, lower alkyl or lower alkoxy; or
R is a carbocyclic group having from 3–7 members, where up to three of which members are heteroatoms selected from oxygen and nitrogen and where any member of the carbocyclic group is unsubstituted or substituted with halogen, lower alkyl, or lower alkoxy;
A and B are the same or different and represent hydrogen, or lower alkyl; and
W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl.

5. A pharmaceutical composition according to claim 2 comprising a compound of the formula:

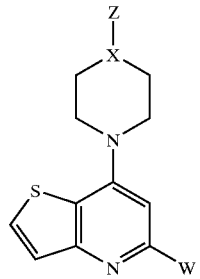

or a pharmaceutically acceptable salt thereof, with at least one carrier, adjuvant or vehicle, wherein:
X is CH, nitroge n, or oxygen;
Z is an electron pair when X is oxygen;
Z is hydrogen, provided that when X is CH, Z is not hydrogen;
Z is aryl, which is unsubstituted or substituted with one or two groups independently selected from lower alkyl, lower alkoxy, or hal ogen; or

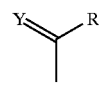

where
Z is
Y is oxygen or sulfur;
R is lower alkyl, hydroxy, lower alkoxy, hydroxyalkyl, or aminoalkyl;
R is aryl or heteroaryl, each of which is mono or disubstituted independently with halogen, thio, hydroxyl, lower alkyl, lower alkoxy, or amino;
R is amino, which is unsubstituted or substituted with one or two groups independently selected from
lower alkyl, hydroxyalkyl, alkoxyalkyl, aminoalkyl, haloalkyl, hydroxy, aminoalkyl, or amidoalkyl;
heteroaryl, arylalkyl or heteroarylalkyl, each of which is unsubstituted or substituted with one or two groups independently selected from halogen, thio, hydroxyl, lower alkyl, lower alkoxy, or amino; or
a carbocyclic group having from 3–7 members, where up to two of which members are heteroatoms selected from oxygen and nitrogen and where any member of the carbocyclic group is unsubstituted or substituted with halogen, lower alkyl or lower alkoxy; or
R is a carbocyclic group having from 3–7 members, wherein up to three of the carbocyclic group are heteroatoms that are independently oxygen or nitrogen and where the carbocyclic group is unsubstituted or substituted with one, two, or three groups that are independently halogen, lower alkyl, or lower alkoxy; and
W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl.

6. A pharmaceutical composition according to claim 2 comprising a compound of the formula:

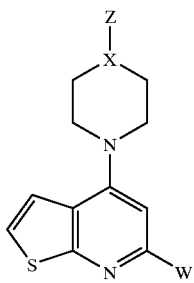

or a pharmaceutically acceptable salt thereof, with at least one carrier, adjuvant or vehicle, wherein:

X is CH, nitrogen, or oxygen;

Z is an electron pair when X is oxygen;

Z is hydrogen, provided that when X is CH, Z is not hydrogen;

Z is aryl, which is unsubstituted or substituted with one or two groups independently selected from lower alkyl, lower alkoxy, or halogen; or

where

Z is

Y is oxygen or sulfur;

R is lower alkyl, hydroxy, lower alkoxy, hydroxyalkyl, or aminoalkyl;

R is aryl or heteroaryl, each of which is mono or disubstituted independently with halogen, thio, hydroxyl, lower alkyl, lower alkoxy, or amino;

R is amino, which is unsubstituted or substituted with one or two groups independently selected from lower alkyl, hydroxyalkyl, alkoxyalkyl, aminoalkyl, haloalkyl, hydroxy, aminoalkyl, or amidoalkyl; heteroaryl, arylalkyl or heteroarylalkyl, each of which is unsubstituted or substituted with one or two groups independently selected from halogen, thio, hydroxyl, lower alkyl, lower alkoxy, or amino; or a carbocyclic group having from 3–7 members, where up to two of which members are heteroatoms selected from oxygen and nitrogen and where any member of the carbocyclic group is unsubstituted or substituted with halogen, lower alkyl or lower alkoxy; or R is a carbocyclic group having from 3–7 members, where up to three of which members are heteroatoms selected from oxygen and nitrogen and where any member of the carbocyclic group is which is unsubstituted or substituted with halogen, lower alkyl, or lower alkoxy; and W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl.

7. A pharmaceutical composition according to claim 2 comprising a compound of the formula:

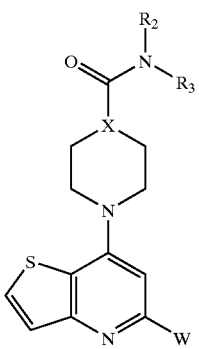

or a pharmaceutically acceptable salt thereof, with at least one carrier, adjuvant or vehicle, wherein:

X is CH, or nitrogen;

W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl; and $R_2$ and $R_3$ are the same or different and represent hydrogen, lower alkyl, hydroxyalkyl, aminoalkyl, alkoxyalkyl, haloalkyl, or amidoalkyl; aryl, arylalkyl, heteroaryl, or heteroarylalkyl each of which is unsubstituted or substituted with one or two groups that are independently halogen, thio, hydroxyl, lower alkyl, lower alkoxy, or amino; or a carbocyclic or carbocyclic($C_1$–$C_6$)alkyl group having from 3–7 members in the carbocyclic portion, where up to two of which members are heteroatoms selected from oxygen and nitrogen and where any member of the carbocyclic group is unsubstituted or substituted with halogen, lower alkyl or lower alkoxy.

8. A pharmaceutical composition according to claim 2 comprising a compound of the formula:

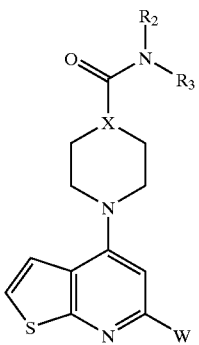

or a pharmaceutically acceptable salt thereof, with at least one carrier, adjuvant or vehicle, wherein:

X is CH, or nitrogen;

W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl; and $R_2$ and $R_3$ are the same or different and represent hydrogen, lower alkyl, hydroxyalkyl, aminoalkyl, alkoxyalkyl, haloalkyl, or amidoalkyl;

aryl, arylalkyl, heteroaryl, or heteroarylalkyl each of which is unsubstituted or substituted with one or two groups independently selected from halogen, thio, hydroxyl, lower alkyl, lower alkoxy, or amino; or a carbocyclic or carbocyclic($C_1$–$C_6$)alkyl group having from 3–7 members in the carbocyclic portion, where up to two of which members are heteroatoms selected from oxygen and nitrogen and where any member of the carbocyclic group is unsubstituted or substituted with halogen, lower alkyl or lower alkoxy.

9. A pharmaceutical composition according to claim 2 comprising a compound of the formula:

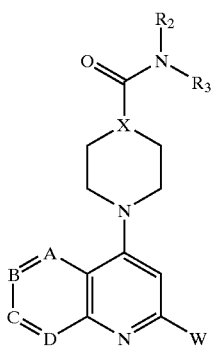

or a pharmaceutically acceptable salt thereof, with at least one carrier, adjuvant or vehicle, wherein:

A, B, C, and D are independently $CR_1$ or nitrogen, provided that no more than two of A, B, C, and D are nitrogen simultaneously;

$R_1$ is hydrogen, lower alkyl, lower alkoxy, halogen, hydroxy, hydroxyalkyl, aminoalkyl, alkoxyalkyl, thio, or arylalkyl;

X is CH, or nitrogen;

W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl; and $R_2$ and $R_3$ are the same or different and represent
hydrogen, lower alkyl, hydroxyalkyl, aminoalkyl, alkoxyalkyl, haloalkyl, or amidoalkyl;
aryl, arylalkyl, heteroaryl, or heteroarylalkyl each of which is unsubstituted or substituted with one or two groups independently selected from halogen, thio, hydroxyl, lower alkyl, lower alkoxy, or amino; or
a carbocyclic or carbocyclic($C_1$–$C_6$)alkyl group having from 3–7 members in the carbocyclic portion, where up to two of which members are heteroatoms selected from oxygen and nitrogen and where any member of the carbocyclic group is unsubstituted or substituted with halogen, lower alkyl or lower alkoxy.

10. A pharmaceutical composition according to claim 2 comprising a compound of the formula:

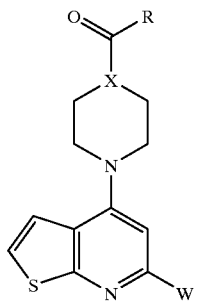

or a pharmaceutically acceptable salt thereof, with at least one carrier, adjuvant or vehicle, wherein:

X is CH, or nitrogen;

R is lower alkyl, hydroxy, lower alkoxy, hydroxyalkyl, or aminoalkyl;

R is aryl, arylalkyl, heteroaryl, or heteroarylalkyl, each of which is unsubstituted or substituted with one or two groups that are independently halogen, thio, hydroxyl, lower alkyl, lower alkoxy, or amino; or R is a carbocyclic group having from 3–7 members, where up to three of which members are heteroatoms selected from oxygen and nitrogen and where any member of the carbocyclic group is unsubstituted or substituted with halogen, lower alkyl, or lower alkoxy; and W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl.

11. A pharmaceutical composition according to claim 2 comprising a compound of the formula:

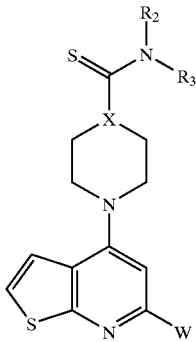

or a pharmaceutically acceptable salt thereof, with at least one carrier, adjuvant or vehicle, wherein:

X is CH, or nitrogen;

W is aryl, heteroaryl, 2- or 3-thienyl, or 2-, 3-, or 4-pyridyl, each of which is unsubstituted or mono or disubstituted independently with halogen, hydroxyl, lower alkyl, lower alkoxy, amino, or mono- or dialkylamino where each alkyl portion is lower alkyl; and $R_2$ and $R_3$ are the same or different and represent
hydrogen, lower alkyl, hydroxyalkyl, aminoalkyl, alkoxyalkyl, haloalkyl, or amidoalkyl;
aryl, arylalkyl, heteroaryl, or heteroarylalkyl each of which is unsubstituted or substituted with one or two groups independently selected from halogen, thio, hydroxyl, lower alkyl, lower alkoxy, or amino; or a carbocyclic or carbocyclic($C_1$–$C_6$)alkyl group having from 3–7 members in the carbocyclic portion, where up to two of which members are heteroatoms selected from oxygen and nitrogen and where any member of the carbocyclic group is unsubstituted or substituted with halogen, lower alkyl or lower alkoxy.

12. A pharmaceutical composition according to claim 2 comprising a compound of formula:

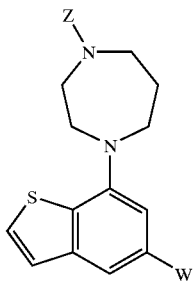

or a pharmaceutically acceptable salt thereof, with at least one carrier, adjuvant or vehicle, wherein:

W is aryl, heteroaryl, 2- or 3-thienyl, or 2-, 3-, or 4-pyridyl, each of which is unsubstituted or substituted with one or two groups that are independently halogen, hydroxyl, lower alkyl, lower alkoxy, amino, or mono- or di lower alkylamino;

Z is hydrogen;

Z is aryl, which is unsubstituted or substituted with one or two groups that are independently lower alkyl, lower alkoxy, or halogen; or

where

Z is

Y is oxygen or sulfur;

R is lower alkyl, hydroxy, lower alkoxy, hydroxyalkyl, or aminoalkyl;

R is aryl, arylalkyl, heteroaryl, or heteroarylalkyl, each of which is unsubstituted or substituted with one or two groups that are independently halogen, thio, hydroxyl, lower alkyl, lower alkoxy, or amino;

R is amino, which is unsubstituted or substituted with one or two groups that are independently lower alkyl, hydroxyalkyl, alkoxyalkyl, aminoalkyl, haloalkyl, hydroxy, aminoalkyl, or amidoalkyl, heteroaryl, $C_3$–$C_7$ cycloalkyl, or $C_3$–$C_7$ carbocyclic, each of which is unsubstituted or substituted with one, two, or three, groups that are independently halogen, lower alkyl or lower alkoxy; or R is a carbocyclic group having from 3–7 members, where one, two, or three carbon atoms are independently replaced by oxygen or nitrogen and where the carbocyclic group is unsubstituted or substituted with one, two, or three groups that are independently halogen, lower alkyl, or lower alkoxy.

13. A pharmaceutical composition according to claim 2 comprising a compound of the formula:

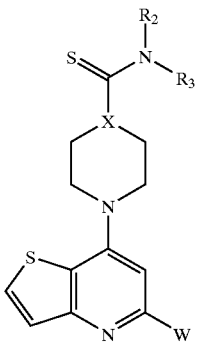

or a pharmaceutically acceptable salt thereof, with at least one carrier, adjuvant or vehicle, wherein:

X is CH, or nitrogen;

W is aryl, heteroaryl, 2- or 3-thienyl, or 2-, 3-, or 4-pyridyl, each of which is unsubstituted or substituted with one or two groups that are independently halogen, hydroxyl, lower alkyl, lower alkoxy, amino, or mono- or di-lower alkylamino; and $R_2$ and $R_3$ are the same or different and represent
hydrogen, lower alkyl, hydroxyalkyl, aminoalkyl, alkoxyalkyl, haloalkyl, amidoalkyl;
aryl, arylalkyl, heteroaryl, or heteroarylalkyl each of which is unsubstituted or substituted with one or two groups that are independently halogen, thio, hydroxyl, lower alkyl, lower alkoxy, or amino; or
a carbocyclic or $C_3$–$C_7$ carbocyclic $C_1$–$C_6$ alkyl group each of which is unsubstituted or substituted with one, two, or three groups that are independently halogen, lower alkyl or lower alkoxy.

14. A method of treating anxiety, sleep disorders, overdose with benzodiazepine drugs or enhancement of memory, said method comprising administering a pharmaceutical composition according to claim 2 to a mammal in need of such treatment.

15. A method according to claim 14 wherein the compound is:

1-(5-Phenyl-thieno[3,2-b]pyridin-7-yl)-piperidine-4-carboxylic acid ethylamide;

1-(5-Phenyl-thieno[3,2-b]pyridin-7-yl)-piperidine-4-carboxylic acid (pyridin-4-ylmethyl)-amide;

(4-Fluoro-phenyl)-{4-[5-(3-methoxy-phenyl)-thieno[3,2-b]pyridin-7-yl]-piperazin-1-yl}-methanone;

7-Morpholin-4-yl-5-phenyl-thieno[3,2-b]pyridine;

7-[1,4]Diazepan-1-yl-5-phenyl-thieno[3,2-b]pyridine;

{4-[5-(3-Methoxy-phenyl)-thieno[3,2-b]pyridin-7-yl]-piperazin-1-yl}-pyridin-4-yl-methanone;

4-(5-Phenyl-thieno[3,2-b]pyridin-7-yl)-piperazine-1-carbothioic acid ethylamide;

1-(2-Phenyl-[1,5]naphthyridin-4-yl)-piperidine-4-carboxylic acid;

1-(5-Phenyl-thieno[3,2-b]pyridin-7-yl)-piperidine-4-carboxylic acid cyclopentylamide;

2-{(N'-[1-(5-Phenyl-thieno[3,2-b]pyridin-7-yl)-piperidine-4-carbonyl]-hydrazino}-acetamide;

1-(5-Phenyl-thieno[3,2-b]pyridin-7-yl)-piperidine-4-carboxylic acid (2-methoxy-ethyl)-amide;

3-(2-Fluoro-phenyl)-1-[1-(5-phenyl-thieno[3,2-b]pyridin-7-yl)-piperidin-4-yl]-propan-1-one;

1-(5-Phenyl-thieno[3,2-b]pyridin-7-yl)-piperidine-4-carboxylic acid (tetrahydro-furan-2-ylmethyl)-amide;

1-[5-(4-Fluoro-phenyl)-thieno[3,2-b]pyridin-7-yl]-piperidine-4-carboxylic acid amide;

1-[5-(4-Fluoro-phenyl)-thieno[3,2-b]pyridin-7-yl]-piperidine-4-carboxylic acid (2-methoxy-propyl)-amide;

1-(6-Phenyl-thieno[2,3-b]pyridin-4-yl)-piperidine-4-carboxylic acid ethylamide; or a pharmaceutically acceptable salt thereof.

16. A pharmaceutical composition according to claim 2 wherein the compound is:

N-Ethyl 1-(6-phenylthieno[2,3-b]pyridin-4-yl)-4-piperidinecarboxamide;

N-Methyl 1-(5-phenylthieno[3,2-b]pyridin-7-yl)-4-piperazinecarboxamide;

1-(5-Phenylthieno[3,2-b]pyridin-7-yl)-4-piperidinecarboxamide;

1-(5-(2-Fluorophenyl)thieno[3,2-b]pyridin-7-yl)-4-piperidinecarboxamide;

N-4-Picolyl-1-(5-phenylthieno[3,2-b]pyridin-7-yl)-4-piperidinecarboxamide;

N-(2-Hydroxyethyl) 1-(5-phenylthieno[3,2-b]pyridin-7-yl)-4-piperidinecarboxamide;

4-Fluorophenyl-1-(5-(3-methoxyphenyl)thieno[3,2-b]pyridin-7-yl))-4-piperazine;

N-Methylhexahydro-4-(5-phenylthieno[3,2-b]pyridin-7-yl)-(1H-1,4-diazepine)-1-carboxamide; or 4-(5-Phenylthieno[3,2-b]pyridin-7-yl)morpholine.

17. A pharmaceutical composition according to claim 2 wherein the compound is:

N-(3-Chloro-n-Propyl) 1-(5-(4-fulorophenyl)thieno[3,2-b]pyridin-7-yl)-4-piperazinecarboxamide;

N-Ethyl 1-(5-(4-fulorophenyl)thieno[3,2-b]pyridin-7-yl)-4-piperazinecarboxamide;

N-Ethyl 1-(5-phenylthieno[3,2-b]pyridin-7-yl)-4-piperazinecarbothioamide;

1-(2-Phenyl-1,5-naphthyridin-4-yl)-4-piperidinecarboxylic acid ethyl ester;

N-Ethyl 1-(2-phenyl-1,5-naphthyridin-4-yl)-4-piperidinecarboxamide;

N-Methyl 1-(5-phenylthieno[3,2-b]pyridin-7-yl)-4-piperidinecarboxamide;

N-Propyl 1-(5-phenylthieno[3,2-b]pyridin-7-yl)-4-piperidinecarboxamide; or 1-(5-Phenylthieno[3,2-b]pyridin-7-yl)-4-piperidinecarboxamide.

18. A pharmaceutical composition according to claim 2 wherein the compound is:

N-t-Butyl 1-(5-phenylthieno[3,2-b]pyridin-7-yl)-4-piperidinecarboxamide;

N-n-Butyl 1-(5-phenylthileno[3,2-b]pyridin-7-yl)-4-piperidinecarboxamide;

N-Cyclopropyl 1-(5-phenylthieno[3,2-b]pyridin-7-yl)-4-piperidinecarboxamide;

N-Cyclopentyl 1-(5-phenylthieno[3,2-b]pyridin-7-yl)-4-piperidinecarboxamide;

N-(2-Aminoethyl) 1-(5-phenylthieno[3,2-b]pyridin-7-yl)-4-piperidinecarboxamide;

N-(2-Ethylaminoethyl) 1-(5-phenylthieno[3,2-b]pyridin-7-yl)-4-piperidinecarboxamide;

N-(2-Dimethylaminoethyl) 1-(5-phenylthieno[3,2-b]pyridin-7-yl)-4-piperidinecarboxamide; or N-Glycinamidyl 1-(5-phenylthieno[3,2-b]pyridin-7-yl)-4-piperidinecarboxamide.

19. A pharmaceutical composition according to claim 2 wherein the compound is:

N-(2-Hydroxyethyl) 1-(5-phenylthieno[3,2-b]pyridin-7-yl)-4-piperidinecarboxamide;

N-(2-Methoxyethyl) 1-(5-phenylthieno[3,2-b]pyridin-7-yl)-4-piperidinecarboxamide;

N-(3-Methoxypropyl) 1-(5-phenylthieno[3,2-b]pyridin-7-yl)-4-piperidinecarboxamide;

N-Benzyl 1-(5-phenylthieno[3,2-b]pyridin-7-yl)-4-piperidinecarboxamide;

N-2-Fluorobenzyl 1-(5-phenylthieno[3,2-b]pyridin-7-yl)-4-piperidinecarboxamide;

N-3-Fluorobenzyl 1-(5-phenylthieno[3,2-b]pyridin-7-yl)-4-piperidinecarboxamide;

N-4-Fluorobenzyl 1-(5-phenylthieno[3,2-b]pyridin-7-yl)-4-piperidinecarboxamide; or N-4-Methylbenzyl 1-(5-phenylthieno[3,2-b]pyridin-7-yl)-4-piperidinecarboxamide.

20. A pharmaceutical composition according to claim 2 wherein the compound is:

N-4-Ethoxybenzyl 1-(5-phenylthieno[3,2-b]pyridin-7-yl)-4-piperidinecarboxamide;

N-4-Pyridylmethyl 1-(5-phenylthieno[3,2-b]pyridin-7-yl)-4-piperidinecarboxamide;

N-2-Thiophenylmethyl 1-(5-phenylthieno[3,2-b]pyridin-7-yl)-4-piperidinecarboxamide;

N-2-Tetrahydrofuranylmethyl 1-(5-phenylthieno[3,2-b]pyridin-7-yl)-4-piperidinecarboxamide;

1-(5-Phenylthieno[3,2-b]pyridin-7-yl)-4-piperidinecarboxylic acid ethyl ester;

1-(5-Phenylthieno[3,2-b]pyridin-7-yl)-4-piperidinecarboxylic acid;

1-(5-(3-Methoxyphenyl)thieno[3,2-b]pyridin-7-yl)-4-piperidinecarboxamide; or

N-Ethyl 1-(5-(3-methoxyphenyl)thieno[3,2-b]pyridin-7-yl)-4-piperidinecarboxamide.

21. A pharmaceutical composition according to claim 2 wherein the compound is;

1-(5-(4-Ethoxyphenyl)thieno[3,2-b]pyridin-7-yl)-4-piperidinecarboxamide;

N-2-Pyridinylmethyl 1-(5-(4-ethoxyphenyl)thieno[3,2-b]pyridin-7-yl)-4-piperidinecarboxamide;

1-(5-(4-Fluorophenyl)thieno[3,2-b]pyridin-7-yl)-4-piperidinecarboxamide;

N-Methyl 1-(5-(4-fluorophenyl)thieno[3,2-b]pyridin-7-yl)-4-piperidinecarboxamide;

N-Ethyl 1-(5-(4-fluorophenyl)thieno[3,2-b]pyridin-7-yl)-4-piperidinecarboxamide;

N-Propyl 1-(5-(4-fluorophenyl)thieno[3,2-b]pyridin-7-yl)-4-piperidinecarboxamide;

N-(2-Aminoethyl) 1-(5-(4-fluorophenyl)thieno[3,2-b]pyridin-7-yl)-4-piperidinecarboxamide;

N-(2-Dimethylaminoethyl) 1-(5-(4-fluorophenyl)thieno[3,2-b]pyridin-7-yl)-4-piperidinecarboxyamide.

22. A pharmaceutical composition according to claim 2 wherein the compound is:

N-(2-Hydroxyethyl) 1-(5-(4-fluorophenyl)thieno[3,2-b]pyridin-7-yl)-4-piperidinecarboxamide;

N-(2-Methoxypropyl) 1-(5-(4-fluorophenyl)thieno[3,2-b]pyridin-7-yl)-4-piperidinecarboxamide;

N-Ethyl 1-(5-(4-pyridyl)thieno[3,2-b]pyridin-7-yl)-4-piperidinecarboxamide;

1-(6-Phenylthieno[2,3-b]pyridin-4-yl)-4-piperidinecarboxylic acid methyl ester;

N-Ethyl 1-(6-Phenylthieno[2,3-b]pyridin-4-yl)-4-piperidinecarboxamide hydrochloride;

5-(4-Fluorophenyl)-7-[4-(1H-imidazol-2-yl)-1-piperidinyl thieno[3,2-b]pyridine;

1-(5-(4-fluorophenyl)thieno[3,2-b]pyridin-7-yl) piperidine-4-carboxamide; or 5-(4-Fluorophenyl)-7-[4-(1H-1,2,4-triazol-3-yl)-1-piperidinyl]thieno[3,2-b]pyridine.

23. A pharmaceutical composition according to claim 2 wherein the compound is:

N-Ethyl 1-(5-phenylthieno[3,2-b]pyridin-7-yl)-4-piperazinecarboxamide;

4-Pyridinylcarbonyl-1-(5-(3-methoxyphenyl)thieno[3,2-b]pyridin-7-yl))-4-piperazine;

N-Ethyl 1-(5-(3-methoxyphenyl)thieno[3,2-b]pyridin-7-yl)-4-piperazinecarboxamide;

N-n-Propyl 1-(5-(4-fluorophenyl)thieno[3,2-b]pyridin-7-yl)-4-piperazinecarboxamide;

N-i-Propyl 1-(5-(4-fluorophenyl)thieno[3,2-b]pyridin-7-yl)-4-piperazinecarboxamide; or N-n-Butyl 1-(5-(4-fluorophenyl)thieno[3,2-b]pyridin-7-yl)-4-piperazinecarboxamide.

* * * * *